United States Patent [19]

Berkelhammer et al.

[11] 4,199,595

[45] Apr. 22, 1980

[54] M-PHENOXYBENZYL AND α-CYANO-M-PHENOXYBENZYL ESTERS OF 2-HALOALKYL (OXY-, THIO-, SULFINYL-, OR SULFONYL)PHENYLALKANOIC ACIDS

[75] Inventors: Gerald Berkelhammer; Venkataraman Kameswaran, both of Princeton, N.J.

[73] Assignee: American Cyanamid Company, Stamford, Conn.

[21] Appl. No.: 890,568

[22] Filed: Mar. 20, 1978

Related U.S. Application Data

[63] Continuation-in-part of Ser. No. 814,600, Jul. 11, 1977, abandoned, which is a continuation-in-part of Ser. No. 728,818, Oct. 1, 1976, abandoned.

[51] Int. Cl.² .................... A01N 9/12; A01N 9/20; C07C 69/76; C07C 121/75

[52] U.S. Cl. .................. 424/304; 260/465 D; 260/465 F; 260/465 G; 260/544 D; 260/544 S; 260/609 R; 424/308; 424/309; 560/9; 560/11; 560/12; 560/23; 560/55; 562/426; 562/429; 562/438; 562/465; 568/635; 568/655

[58] Field of Search .................. 260/465 D; 560/105, 560/9, 11, 55; 424/304, 308

[56] References Cited

U.S. PATENT DOCUMENTS 4,058,622  11/1977  Fujimoto et al. .................. 424/308

*Primary Examiner*—Dolph H. Torrence
*Attorney, Agent, or Firm*—H. G. Jackson

[57] ABSTRACT

The invention is m-phenoxybenzyl esters of 2-haloalkyl-(oxy-, thio-, sulfinyl-, or sulfonyl)phenylalkanoic acids which are useful insecticidal and acaricidal agents.

29 Claims, No Drawings

M-PHENOXYBENZYL AND α-CYANO-M-PHENOXYBENZYL ESTERS OF 2-HALOALKYL (OXY-, THIO-, SULFINYL-, OR SULFONYL)PHENYLALKANOIC ACIDS

This application is a continuation-in-part of application Ser. No. 814,600 filed July 11, 1977 and now abandoned, which in turn is a continuation-in-part of now abandoned application Ser. No. 728,818 filed Oct. 1, 1976.

The closest art of which we are aware has been disclosed in South African Patent Application No. 73/4462, assigned to Sumitomo Chemical Company Limited. The applicants generically describe literally tens of thousands of phenylacetic acid esters including 3'-phenoxybenzyl-α-isopropyl-4-methoxyphenylacetate; 3'-phenoxybenzyl-α-isopropyl-3-methoxyphenylacetate; 3'-phenoxybenzyl-α-isopropyl-4-chlorophenylacetate; 3'-phenoxybenzyl-α-isopropyl-4-methylphenylacetate; 3'-phenoxybenzyl-α-isopropyl-3-chlorophenylacetate and 3'-phenoxybenzyl-α-isopropyl-4-fluorophenylacetate. They indicate that many of their compounds are effective pesticidal agents and useful for the control of a variety of insects and mites. The applicants do not, however, describe the m-phenoxybenzyl esters of 2-haloalkyl(oxy-, thio-, sulfinyl-, or sulfonyl)phenylalkanoic acids which are the subject of the present invention; nor do they provide a synthesis applicable to the preparation of the compounds.

Surprisingly, we have found that the compounds of the present invention are not only effective insecticidal agents but are also highly effective ixodicidal agents. Moreover, the compounds of our invention are animal systemic insecticidal and ixodicidal agents. The compounds can be used effectively to protect domestic, laboratory and farm animals from attack by insects and ticks. The compounds of this invention also exhibit superior residual ixodicidal and insecticidal activity when compared with known pyrethroids such as permethrin, phenothrin, allethrin, or the like, and are outstandingly effective for control of tobacco budworm and mosquitoes.

The invention is m-phenoxybenzyl esters of 2-haloalkyl(oxy-, thio-, sulfinyl-, or sulfonyl)phenylalkanoic acids represented by the formula:

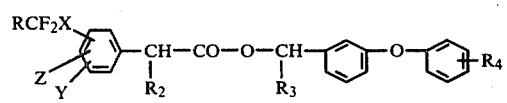

wherein RCF$_2$X—, Y and Z, are all meta or para to the carbon to which the alkanoic acid ester group is attached, and X is O, S, SO or SO$_2$; Y and Z are each H, Cl, F, Br, NO$_2$, CH$_3$ or OCH$_3$; R is H, F, Cl, CHF$_2$ or CF$_3$; R$_2$ is ethyl, n-propyl, isopropyl, isopropenyl or t-butyl; R$_3$ is H, CN or —C≡CH, and R$_4$ is H, F, Cl, CH$_3$ or OCH$_3$.

Preferred compounds can be shown by the structure:

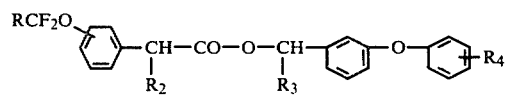

wherein RCF$_2$O— is meta or para to the carbon to which the alkanoic acid ester group is attached; R is H or F; R$_2$ is ethyl, n-propyl or isopropyl; R$_3$ is H, CN or —C≡CH and R$_4$ is H, F, Cl, CH$_3$ or OCH$_3$. Most preferred compounds are represented by the compounds having the preferred compound structure, but R is H or F; R$_2$ is isopropyl; R$_3$ is CN and R$_4$ is H or F. The invention is also a method for controlling insects and acarina by contacting the insects and acarina, their habitat, breeding grounds and/or their food supply, with an insecticidally or acaricidally effective amount of a m-phenoxybenzyl ester of 2-haloalkyl(oxy-, thio-, sulfinyl-, or sulfonyl)phenylalkanoic acids. The invention includes a method for protecting agronomic crops, either growing or harvested, and homothermic animals from attack by insects and/or acarina by treating the crops and/or animals with an insecticidally or acaricidally effective amount of the above-identified m-phenoxybenzyl ester of 2-haloalkyl(oxy-, thio-, sulfinyl-, or sulfonyl)phenylalkanoic acids.

Advantageously, the m-phenoxybenzyl esters of 2-haloalkyl(oxy-, thio-, sulfinyl-, or sulfonyl)phenylalkanoic acids, depicted by formula I, can be prepared by reacting an alpha substituted 2-haloalkyl(oxy-, thio-, sulfinyl-, or sulfonyl)phenylacetyl halide (II), preferably chloride, with a m-phenoxybenzyl alcohol (III). The reaction is generally conducted in the presence of a solvent such as diethyl ether, benzene, or toluene, at a temperature between about 10° C. and 30° C. in the presence of an acid acceptor. Among the acid acceptors that can be employed are the tertiary organic amines, trimethylamine, triethylamine and pyridine. This reaction can be illustrated as follows:

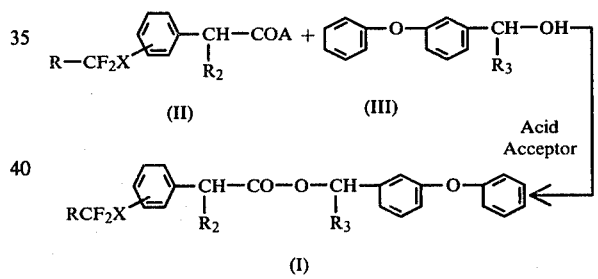

wherein RCF$_2$X is meta or para to the carbon to which the alkanoic acid group is attached, and X is O, S, SO, or SO$_2$ and wherein R is H, F, Cl, CHF$_2$ or CF$_3$; R$_2$ is ethyl, n-propyl, isopropyl, isopropenyl, or t-butyl; R$_3$ is H or CN and A is halogen, preferably chlorine.

With regard to the compounds of the present invention is depicted by formula I, it should also be understood that various optical isomers of the above-identified compounds do result from the preparations described.

For example, in the synthesis of formula I esters, wherein R$_3$ is hydrogen, a chiral center is present at R$_2$ and d and l isomeric pairs are formed. Also, α-cyano substitution at R$_3$ introduces an additional chiral center, thus allowing for an additional d, l pair.

For example, it has been found that when α-isopropyl-4-trifluoromethoxyphenylacetic acid is mixed with from about 0.5 to 1.0 molar equivalent of (—)-α-phenethylamine in a suitable solvent such as ethanol or aqueous ethanol, that the salt of the (+)-acid is precipitated. When acidified, this salt releases the acid which is generally in excess of 85% of the (+)-isomer. Higher resolution may be achieved by recrystallization of the (—)-

α-phenethylamine salt or by repeating the resolution process with fresh (−)-α-phenethylamine. The m-phenoxybenzyl or α-cyano-m-phenoxybenzyl esters of the completely resolved (+)-α-isopropyl-4-trifluoromethoxyphenylacetic acid are found to be about twice as effective insecticidally as the respective esters prepared from the racemic acid. In the case of the α-cyano-m-phenoxybenzyl ester, an additional increase in activity is obtained when the appropriate optically active α-cyano-m-phenoxybenzyl alcohol is used in the ester-forming step.

The α-substituted 2-haloalkyl(oxy-, thio-, sulfinyl-, or sulfonyl)phenylacetyl halides (II) where $R_2$ is ethyl, n-propyl, or isopropyl, can be prepared using the appropriate toluene (IV) as a starting material. The process for the preparation involves five steps, the first of which is the halogenation of the toluene (IV) with bromine, chlorine, N-bromosuccinimide (NBS), or the like. This reaction is preferably conducted in the presence of an inert organic solvent such as carbon tetrachloride, and a radical initiator such as light, benzoyl peroxide, or azo-bis-isobutyronitrile, to yield the benzyl halide (V). The formula V benzyl halide is then converted to the corresponding phenylacetonitrile (VI) by reaction with sodium or potassium cyanide in the presence of dimethylsulfoxide (DMSO), ethanol, or the like, at an elevated temperature. This (substituted phenyl)acetonitrile (VI) is then readily alkylated when treated with an alkyl halide in the presence of base and an inert organic solvent; crown ethers have been found to be useful catalysts in this reaction. The α-alkyl(substituted phenyl)acetonitrile formed in the above reaction is depicted by formula VII and hydrolysis of this formula VII α-alkyl(substituted phenyl)acetonitrile, using an alkali metal hydroxide in the presence of an alkylene glycol and water, yields the α-alkyl(substituted phenyl)acetic acid, shown as formula VIII. Treatment of the formula VIII acid with thionyl chloride, thionyl bromide, or the like, preferably in the presence of an aromatic solvent such as benzene or toluene, then yields the α-alkyl(substituted phenyl)acetyl halide (II), which is reacted with the m-phenoxybenzyl alcohol (III) or α-cyano-m-phenoxybenzyl alcohol to yield the desired m-phenoxybenzyl ester of α-cyano-m-phenoxybenzyl ester of the 2-haloalkyl(oxy-, thio-, sulfinyl-, or sulfonyl)phenylalkanoic acids (I).

These reactions are graphically illustrated in Flow Diagram I below.

FLOW DIAGRAM I

Preparation of m-Phenoxybenzyl Esters of 2-Haloalkyl(oxy-, thio-, sulfinyl-, or sulfonyl)phenylalkanoic Acids

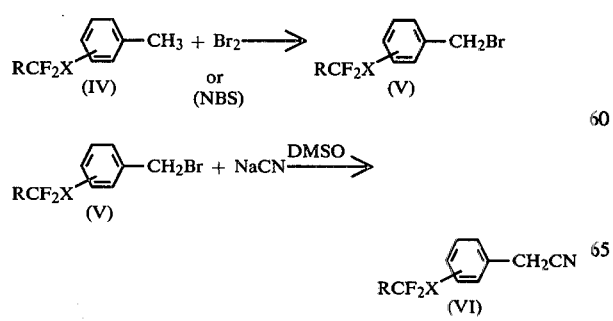

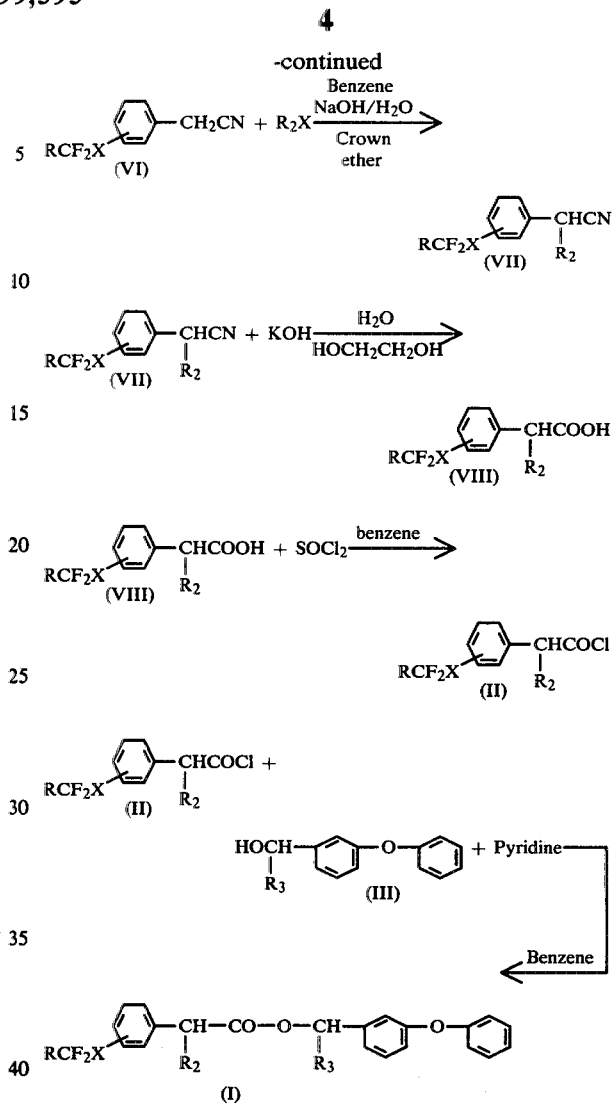

As an alternative to the benzyl bromide (V), shown in Flow Diagram I, where products are to be limited to para-substitution, the appropriate haloalkyl(oxy- or thio-)benzene (IX) may be chloromethylated using a mixture of para-formaldehyde or trioxane with zinc chloride and dry hydrogen chloride to afford the benzyl chloride (X) which can then be used in place of V for completion of the synthesis to I. This modification is illustrated as follows:

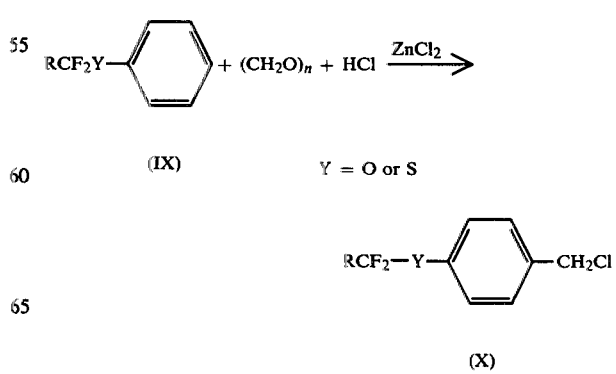

Preparation of the m-phenoxybenzyl and α-cyano-m-phenoxybenzyl esters of α-alkyl-3(or 4)-trifluoromethoxyphenyl acetic acid can also be accomplished by a sequence beginning with the alkylation of m- or p-methoxyphenylacetonitrile, using an alkyl halide in the presence of a crown ether and base. It is, of course, obvious that when the m-methoxyphenylacetonitrile is used in this reaction the α-alkyl-3-methoxyphenylacetonitrile is obtained, and when the p-isomer is employed the α-alkyl-4-methoxyphenylacetonitrile is obtained. It will, likewise, become apparent from the following discussion that the location of the methoxy group on this phenylacetonitrile starting material determines the position of the trifluoromethoxy substituent in the final product.

The α-alkyl-3(or 4)-methoxyphenylacetonitrile, referred to above, is converted to the α-alkyl-3(or 4)-hydroxyphenylacetonitrile by treatment with boron tribromide, preferably in the presence of a solvent such as methylene chloride. Treatment of the thus-formed phenol with thiophosgene and base in the presence of a solvent such as chloroform, then yields the chlorothio ester of O-[m- or p-(1-cyano-2-methylpropyl)phenyl]-formic acid. This ester is converted to the α-alkyl-3(or 4)-trifluoromethoxyphenylacetonitrile with molybdenum hexafluoride, and this compound is then hydrolyzed to the corresponding α-alkyl-3(or 4)-trifluoromethoxyphenylacetic acid by reaction with ethylene glycol in the presence of an alkali metal hydroxide and water.

Treatment of the α-alkyl-3(or 4)-trifluoromethoxyphenylacetic acid with thionyl chloride in the presence of an aromatic solvent such as benzene or toluene, yields the corresponding acid chloride which reacts with m-phenoxybenzyl alcohol or α-cyano-m-phenoxybenzyl alcohol to give the desired m-phenoxybenzyl or α-cyano-m-phenoxybenzyl α-alkyl-3(or 4)-trifluoromethoxyphenylacetate.

These reactions are graphically illustrated in Flow Diagram II below.

FLOW DIAGRAM II

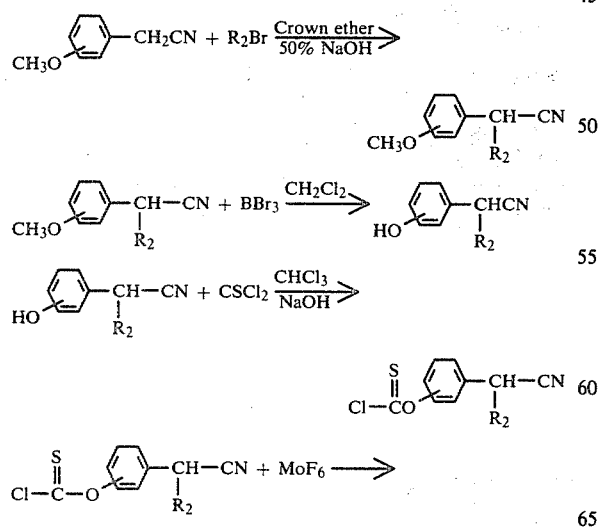

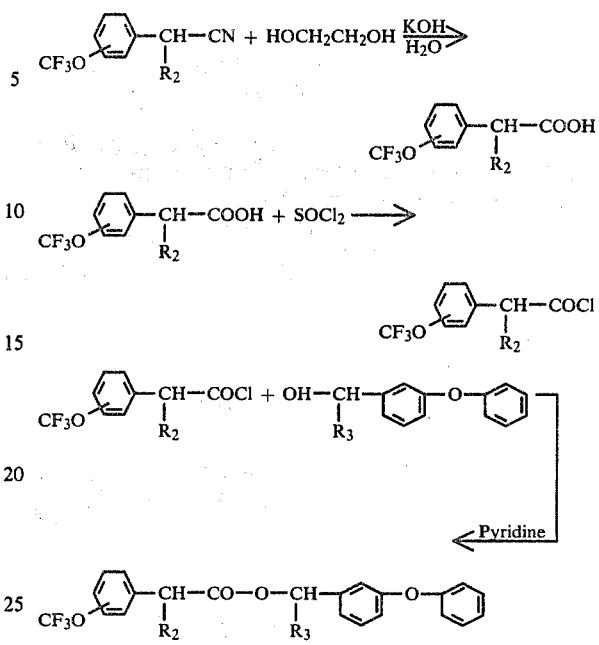

In the reactions set forth on Flow Diagram II, $R_2$ is ethyl, n-propyl or isopropyl, and $R_3$ is hydrogen or cyano.

Whereas Flow Diagram I has general application for the preparation of many compounds of this disclosure as described, it is found that in the alkaline hydrolysis of the nitriles for those examples in which $RCF_2X$— is $HCF_2O$— or $HCF_2S$— that the $HCF_2$— radical can be lost. However, we have found that it may be reintroduced by reacting the appropriate phenol or thiophenol with chlorodifluoromethane in a mixture of aqueous alkali and dioxane.

The actual synthesis of those examples incorporating the $HCF_2O$— group is best demonstrated by the Flow Diagram III in which the appropriate α-alkyl-3(or 4)-methoxyphenylacetonitrile (as shown in Flow Diagram II) is converted to the α-alkyl-3(4)-hydroxyphenylacetic acid using hydrobromic acid. Treatment with chlorodifluoromethane in aqueous alkali and dioxane affords the α-alkyl-3(4)-difluoromethoxyphenylacetic acids. These acids are converted to the desired m-phenoxybenzyl or α-cyano-m-phenoxybenzyl esters, as described in Flow Diagram II.

FLOW DIAGRAM III

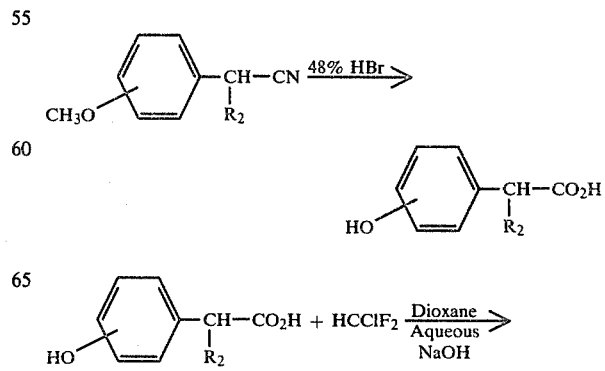

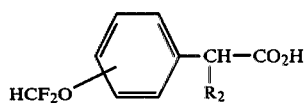

It is also to be noted that although the procedure outlined in Flow Diagram I is suitable for the preparation of most examples where X=

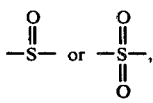

it is frequently better to prepare the final acids (VIII) or esters (I) in which X=—S— and then to oxidize the sulfur atom to the desired

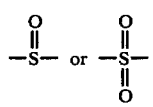

analog through the use of appropriate oxidizing agents such as m-chloroperbenzoic acid, sodium periodate, or hydrogen peroxide.

To prepare those compounds of structure I in which $R_2$ is t-butyl, the following reaction sequence is used, starting with appropriate meta- or para-substituted aldehyde:

(1) reaction with t-butyl magnesium chloride;
(2) conversion of the neopentyl alcohol to the chloride using thionyl chloride;
(3) preparation of the Grignard reagent from the chloride using magnesium in tetrahydrofuran; and
(4) carboxylation with carbon dioxide.

The sequence is further exemplified by the synthesis of α-t-butyl-3(or 4)-trifluoromethoxyphenylacetic acid as illustrated in Flow Diagram IV. The acids can be converted to the corresponding esters, as illustrated in Flow Diagram I.

FLOW DIAGRAM IV

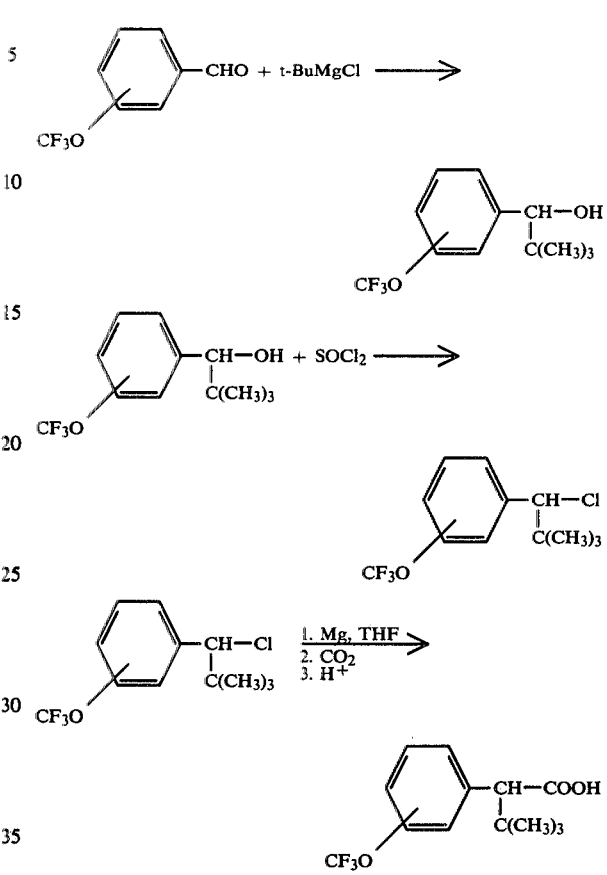

For those compounds of structure I in which $R_2$ is isopropenyl, the introduction of the α-isopropenyl group can be accomplished by the following sequence of reactions using the appropriate meta- or para-substituted-phenylacetic acid:

(1) reaction with two equivalents of isopropyl magnesium chloride and acetone;
(2) conversion of the hydroxy acid to the ester; and
(3) dehydration of the hydroxy ester with $P_2O_5$. The synthesis is further exemplified by the preparation of m-phenoxybenzyl α-isopropenyl-4(or 3)-trifluoromethoxyphenylacetate as illustrated in Flow Diagram V.

FLOW DIAGRAM V

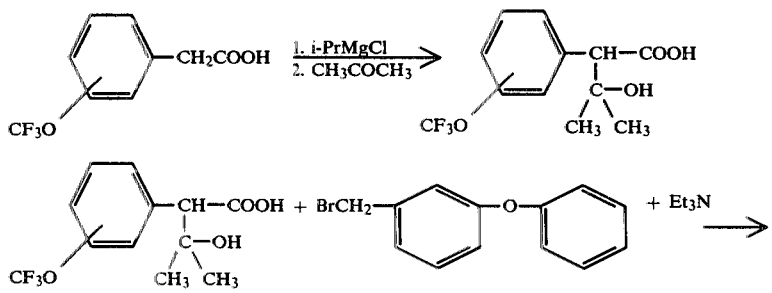

-continued

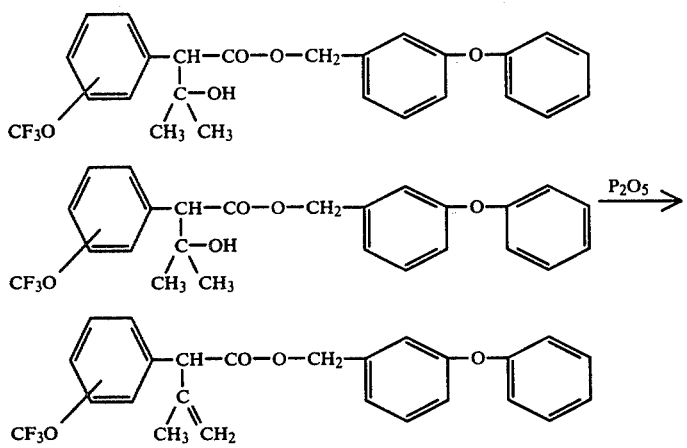

With respect to the formation of the α-cyano-m-phenoxybenzyl ester products by the procedures illustrated in either Flow Diagram I or II, it is not necessary to isolate the α-cyano-m-phenoxybenzyl alcohol precursor. It is equally satisfactory or more satisfactory to allow a mixture of m-phenoxybenzaldehyde, an alkali cyanide such as sodium cyanide, and the appropriate α-substituted 2-haloalkyl(oxy-, thio-, sulfinyl-, or sulfonyl)phenylacetyl halide to react together in one step to form the final α-cyano ester.

Flow diagram VI illustrates the preparation of the mono and disubstituted haloalkyl(oxy-, thio-, sulfinyl and sulfonyl)phenylalkanoic acid-m-phenoxy-m-phenoxybenzyl esters of the invention exemplified in Examples 40–68, below.

FLOW DIAGRAM VI

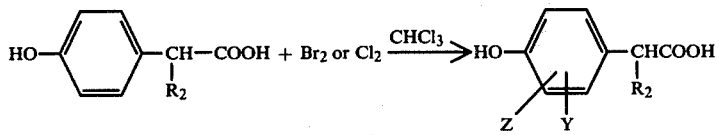

where Z and Y are H, Br or Cl

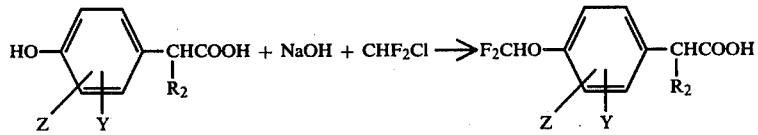

where Z and Y are H, Br or Cl

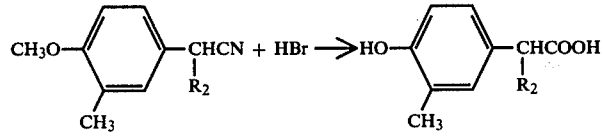

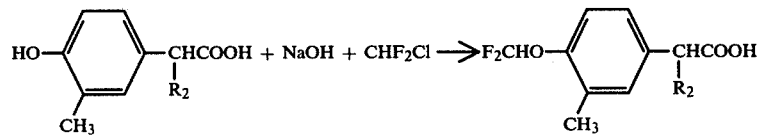

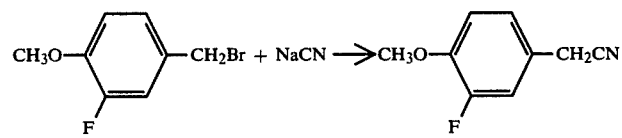

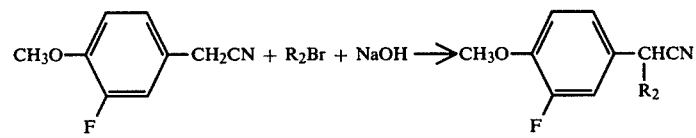

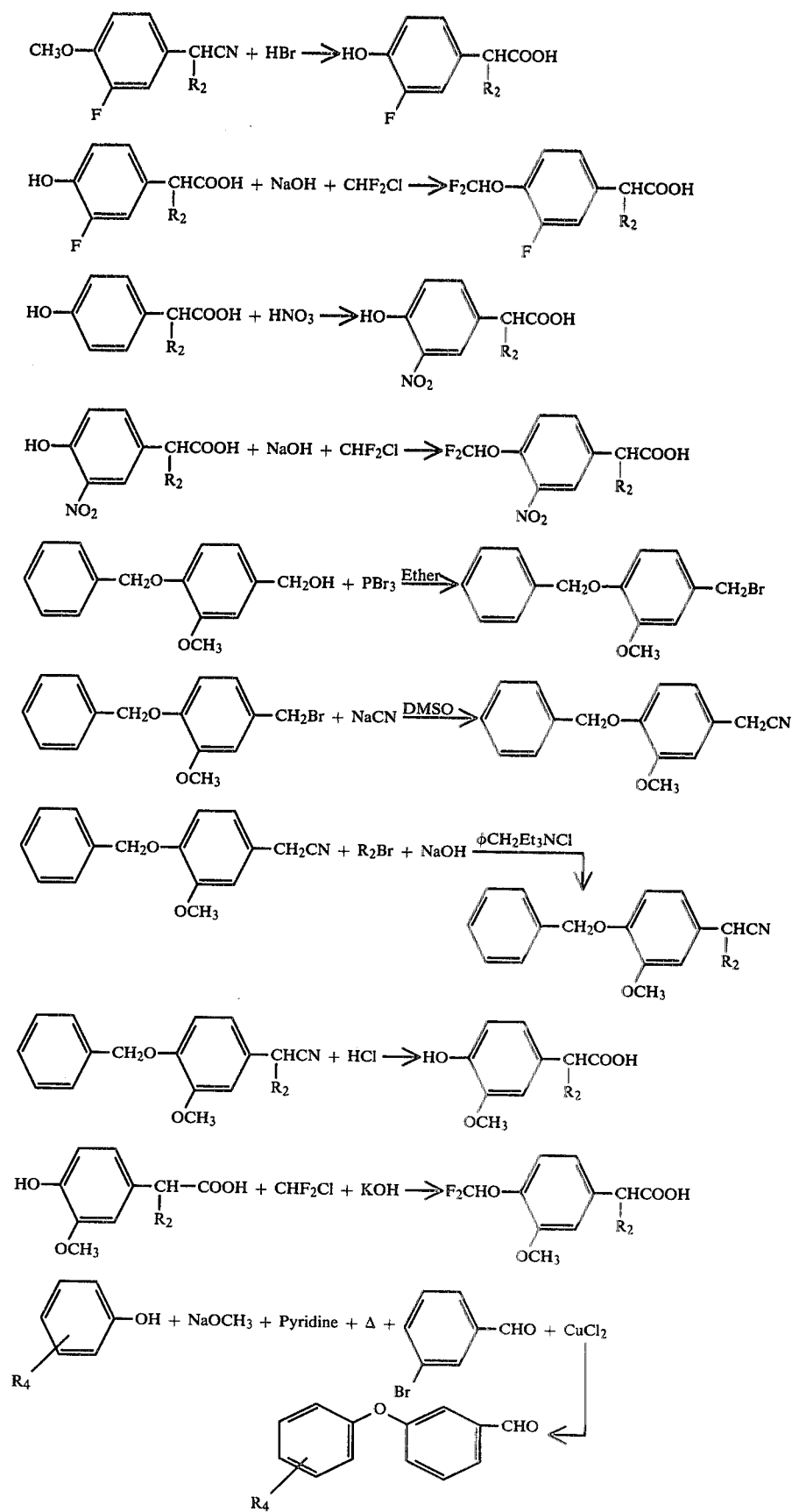

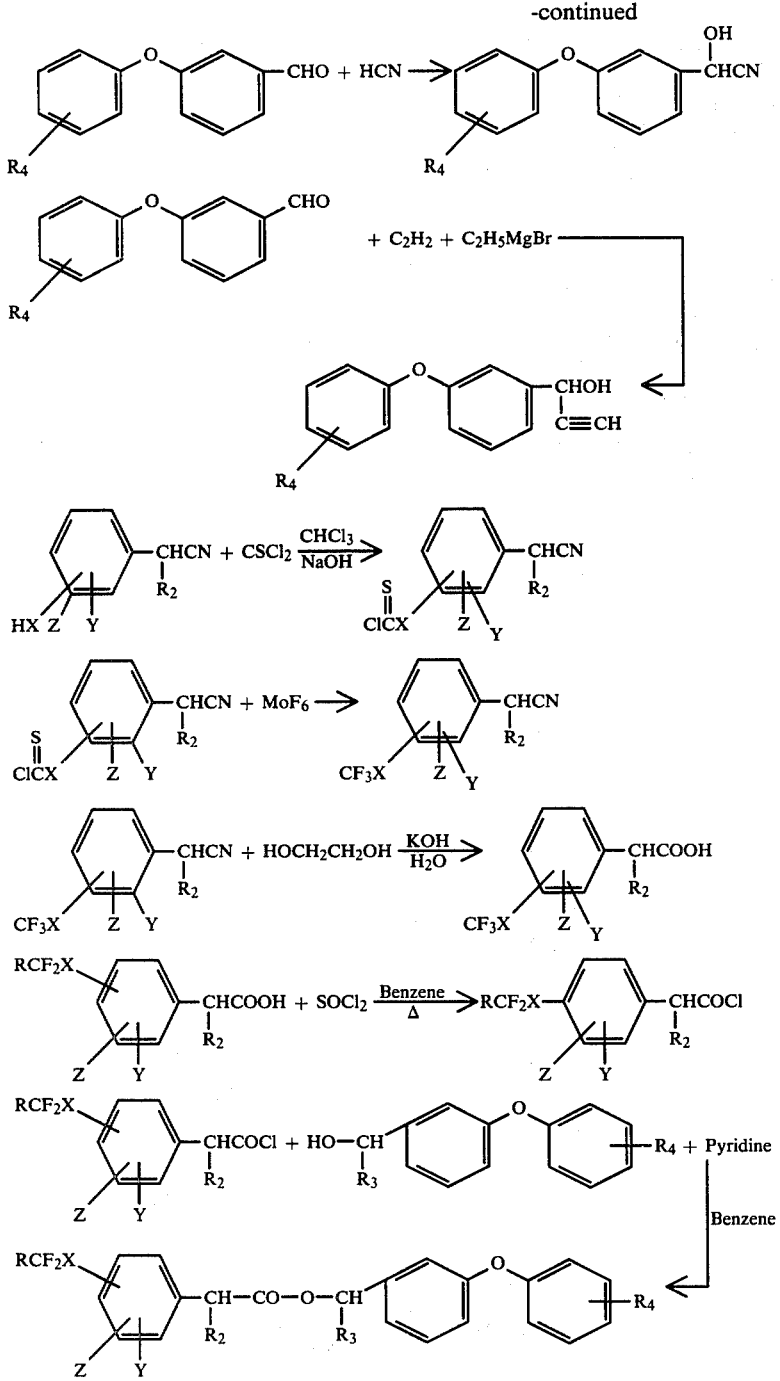

The compounds of the invention are highly effective as contact and stomach poisons for ixodide ticks and for a wide variety of insects, particularly Dipterous, Lepidopterous, Coleopterous and Homopterous insects. They are unusual among pyrethroids, in that they exhibit a very extended residual insecticidal activity on plant tissue, they are effective in the soil, and are surprisingly effective for the control of ixodidae and the protection of animals against attack by insects and ixodidae when administered to the animals orally or parenterally or applied thereto as a topical insecticidal or acaricidal formulation. They do not require admixture with a stabilizing agent to achieve insecticidal and acaricidal compositions having stabilized effects; however, they may be used in combination with other biological chemicals; for example, pyrethroid synergists such as piperonyl butoxide, sesamex or n-octyl sulfoxide of isosafrole. They may also be used in combination with conventional insecticides such as the phosphates, carbamates, formamidines, chlorinated hydrocarbons or halobenzoylureas. To achieve control of insects, including soil insects, which attack growing plants and/or harvested crops, including stored grain, the insecticidal compounds of this invention may be applied to the foliage of plants, the insect's habitat and/or the insect's food supply. Generally, the active compound is applied in the form of a dilute liquid spray; however, it may also be applied as an aerosol, a dust, a granular, or a wettable powder formulation.

Liquid sprays which are particularly useful are oil sprays and emulsifiable concentrates which can be further diluted for application. While they are, respectively, prepared as liquid concentrates; for convenience in handling and shipping, these formulations are usually dispersed in water at the site of their use and then applied as a dilute spray to the plant foliage, soil or surface of the area being treated.

A typical emulsifiable concentrate useful for protecting a variety of crops such as cereals, cole crops, cucurbits, corn, cotton, tobacco, soybeans, ornamentals, shrubs, and the like, may comprise about 20% by weight of the active agent; 4% by weight of an emulsifying agent, conventionally employed in the preparation of pyrethroid formulations; 4% by weight of a surfactant; 25% by weight of an organic solvent such as cyclohexanone; and about 47% by weight of a petroleum solvent having a minimum aromatic content of about 83 volume %.

For use as animal systemic insecticidal and acaricidal agents, the compounds of this invention can be administered to the animal host either orally or parenterally. When given orally, it may be in any convenient form designed for oral administration such as a bolus, capsule, tablet or as an oral drench. The active agent may also be incorporated in an edible animal feedstuff such as a nutritionally balanced diet containing from 0.0001% to 0.1%, and preferably 0.001% to 0.05% by weight of feed of the active compound.

If desired, the systemic insecticidal and acaricidal agent may be introduced into the body of the animal by subcutaneous, intramuscular or intraperitoneal injection, such that it may be distributed through the animal's body by the action of the animal's circulatory system. In practice, the systemic agent may be dissolved or dispersed in a pharmaceutically acceptable carrier such as water, propylene glycol, vegetable oil, glycerol formal, or the like, for administration.

Advantageously, the systemic agents have a good margin of safety and are effective for protecting a variety of animals, particularly livestock and domestic animals such as cattle, sheep, horses, dogs, cats, and the like, from attack by fleas, mosquitoes, flies, ticks, and the like.

Among the compounds of this invention which are useful as insecticidal and acaricidal agents are:

m-Phenoxybenzyl α-isopropyl-4-trifluoromethoxyphenylacetate;
α-Cyano-m-phenoxybenzyl α-isopropyl-4-trifluoromethoxyphenylacetate;
α-Cyano-m-phenoxybenzyl α-isopropyl-3-trifluoromethoxyphenylacetate;
α-Cyano-m-phenoxybenzyl α-isopropyl-4-chlorodifluoromethoxyphenylacetate;
m-Phenoxybenzyl α-isopropyl-4-(1,1,2,2-tetrafluoroethoxy)phenylacetate;
α-Cyano-m-phenoxybenzyl α-isopropyl-4-pentafluoroethoxyphenylacetate;
m-Phenoxybenzyl α-ethyl-3-trifluoromethoxyphenylacetate;
α-Cyano-m-phenoxybenzyl α-n-propyl-4-chlorodifluoromethoxyphenylacetate;
α-Cyano-m-phenoxybenzyl α-t-butyl-4-trifluoromethoxyphenylacetate;
α-Cyano-m-phenoxybenzyl α-isopropyl-4-difluoromethoxyphenylacetate;
α-Cyano-m-phenoxybenzyl α-isopropyl-4-trifluoromethylthiophenylacetate;
m-Phenoxybenzyl α-ethyl-4-trifluoromethylsulfinylphenylacetate;
α-Cyano-m-phenoxybenzyl α-isopropyl-3-difluoromethylsulfonylphenylacetate;
α-Cyano-m-phenoxybenzyl α-ethyl-4-trifluoromethoxyphenylacetate;
α-Cyano-m-phenoxybenzyl α-isopropyl-4-trifluoromethoxyphenylacetate;
m-Phenoxy α-isopropyl-3-bromo-4-difluoromethoxyphenylacetate;
α-Cyano-m-phenoxybenzyl α-isopropyl-3-chloro-4-difluoromethoxyphenylacetate;
m-Phenoxybenzyl α-isopropyl-3-chloro-4-difluoromethoxyphenylacetate;
α-Cyano-m-phenoxybenzyl α-isopropyl-3-bromo-4-difluoromethoxyphenylacetate;
m-Phenoxybenzyl α-isopropyl-3,5-dichloro-4-difluoromethoxyphenylacetate;
α-cyano-m-phenoxybenzyl α-isopropyl-3-methyl-4-difluoromethoxyphenylacetate;
α-cyano-m-phenoxybenzyl α-isopropyl-3-fluoro-4-difluoromethoxyphenylacetate;
α-Cyano-m-phenoxybenzyl α-isopropyl-3-nitro-4-difluoromethoxyphenylacetate;
α-Cyano-m-phenoxybenzyl α-isopropyl-3-methoxy-4-difluoromethoxyphenylacetate;
α-Ethynyl-m-phenoxybenzyl α-isopropyl-4-trifluoromethoxyphenylacetate;
(±)-α-Cyano-m-phenoxybenzyl (±)-α-isopropyl-4-difluoromethoxyphenylacetate and
(±)-α-Cyano-m-phenoxybenzyl (±)-α-isopropyl-4-trifluoromethoxyphenylacetate.

The invention is further described by the examples set forth below.

EXAMPLE 1

Preparation of p-(1,1,2,2-Tetrafluoroethoxy)toluene

For one hour, tetrafluoroethylene and nitrogen are bubbled into a magnetically stirred mixture of 10.8 g (0.100 mol) of p-cresol, 1.67 g (1.67 g (1.43 g real, 0.0255 mol) of potassium hydroxide pellets, and 70 ml of dried dimethylformamide (DMF) maintained at 68° C. After dilution with 250 ml of water, the reaction mixture is extracted with 100 ml of ether. The ether solution is washed with 200 ml of 5% sodium hydroxide and twice with 400 ml of water. The ether solution is dried, filtered, and then rotary evaporated to give 18.14 g (87%) of p-(1,1,2,2-tetrafluoroethoxy)toluene.

Analysis calculated for $C_9H_8F_4O$: C, 51.93%; H, 3.87%; F, 36.51%. Found: C, 52.06%; H, 3.76%; F, 41.52%.

EXAMPLE 2

Preparation of p-(1,1,2,2-Tetrafluoroethoxy)benzyl bromide

A mechanically stirred mixture of 118.45 g (0.569 mol) of p-(1,1,2,2-tetrafluoroethoxy)toluene, 123.00 g (0.691 mol, 121 mol %) of N-bromosuccinimide (NBS), 1.00 g (4.12 mol, 0.73 mol %) of benzoyl peroxide, and 350 ml of carbon tetrachloride is refluxed for 2.25 hours. After cooling, the reaction mixture is diluted with 350 ml of carbon tetrachloride, filtered to remove the solids, dried with sodium sulfate, filtered, and then evaporated, using a rotary evaporator to give 160.99 g (99%) of a clear red oil. This product is used as is in the subsequent reactions. Infrared and NMR show the product to be p-(1,1,2,2-tetrafluoroethoxy)benzyl bromide.

EXAMPLE 3

Preparation of p-(1,1,2,2-Tetrafluoroethoxy)phenylacetonitrile

Over a period of 40 minutes, a hot solution of 75.1 g (1.15 mol) of potassium cyanide in 140 ml of water is added to a mechanically stirred 75° C. solution of 160.99 g (0.561 mol) of p-(1,1,2,2-tetrafluoroethoxy)benzyl bromide and 500 ml of anhydrous 2B alcohol. The resulting mixture is refluxed for 1.75 hours. After sitting overnight the reaction mixture is poured into 500 ml of cold water and 400 ml of ether. The combined ether solutions are washed twice with 500 ml of water, dried with sodium sulfate, filtered, and then evaporated on a rotary evaporator to give 114.95 g of an oil. A vacuum distillation of this oil gives, as one distillation fraction, 37.10 g (28%) of the nitrile, boiling point 85° C. to 100° C. at 0.29 mm Hg.

EXAMPLE 4

Preparation of α-Isopropyl-p-(1,1,2,2-tetrafluoroethoxy)-phenylacetonitrile

A mixture of 39.85 g (0.171 mol) of p-(1,1,2,2-tetrafluoroethoxy)phenylacetonitrile, 3.71 g (9.96 mmol, 5.8 mol %) of dicyclohexyl-18-crown-6, 22.0 ml (28.8 g, 0.234 mol) of 2-bromopropane, 55 ml of benzene, and 55 ml of 50% sodium hydroxide is stirred for 45 minutes during which there is an exotherm from 25° C. to 43° C. The reaction mixture is then heated at 45° C. for 16.5 hours. After dilution with 200 ml of water, the reaction mixture is extracted with 200 ml of ether. The ether solution is washed with 400 ml of 12% hydrochloric acid, 200 ml of 5% hydrochloric acid, and 300 ml of water. The ether solution is dried with sodium sulfate, filtered, and then evaporated to give 47.13 g of an oil. This oil is vacuum distilled to give 34.83 g (74%), boiling point 83° C. to 85° C. at 0.055 to 0.090 mm Hg.

Analysis calculated for $C_{13}H_{13}F_4NO$: C, 56.73%; H, 4.76%; N, 5.09%; F, 27.61%. Found: C, 56.12%; H, 4.85%; N, 4.99%; F, 34.07%.

EXAMPLE 5

Preparation of 3-Methyl-2-[p-(1,1,2,2-tetrafluoroethoxy)phenyl]-butyric acid

A stirred mixture of 48.0 g (24.0 g real, 0.60 mol) of 50% sodium hydroxide, 21.78 g (0.0791 mol) of α-isopropyl-p-(1,1,2,2-tetrafluoroethoxy)phenylacetonitrile, and 240 ml of ethylene glycol is heated at 135° C. for 12 hours. After dilution with 600 ml of water the reaction mixture is washed twice with 100 ml of ether. The water layer is acidified with concentrated hydrochloric acid and then extracted twice with 300 ml of ether. The ether solution is washed twice with 500 ml of water, dried with sodium sulfate, filtered, and then evaporated to give 20.74 g (89%) of a brown solid, melting point 92° C. to 97° C. (hexane).

Analysis calculated for $C_{13}H_{14}F_4O_3$: C, 53.06%; H, 4.80%; F, 25.83%. Found: C, 53.04%; H, 4.79%; F, 25.93%.

EXAMPLE 6

Preparation of 3-Methyl-2-[p-(1,1,2,2-tetrafluoroethoxy)phenyl]butyryl chloride

A stirred mixture of 20.00 g (0.0680 mol) of 3-methyl-2-[p-(1,1,2,2-tetrafluoroethoxy)phenyl]butyric acid, 20.00 ml (33.2 g, 0.280 mol) of thionyl chloride (Baker), and 75 ml of dried benzene is refluxed for 4 hours. The reaction mixture is then evaporated and the resulting residue is diluted with 50 ml of benzene and again evaporated to give 22.46 g (106%) of a clear dark brown liquid. This product is used as is in the subsequent reactions. The liquid is examined by infrared analysis and determined to be the above-named product.

EXAMPLE 7

Preparation of m-Phenoxybenzyl α-isopropyl-4-(1,1,2,2-tetrafluoroethoxy)phenylacetate To a stirred mixture of 6.81 g (0.0340 mol) of m-phenoxybenzyl alcohol, 3.0 ml (2.95 g, 0.0372 mol) of dried pyridine, and 20 ml of methylene chloride is added over a period of 20 minutes a 20 ml methylene chloride solution of 10.6 g (0.034 mol) of 3-methyl-2-[p-(1,1,2,2-tetrafluoroethoxy)phenyl]butyryl chloride. The reaction mixture is stirred at room temperature for 66 hours and then diluted with 200 ml of ether. The ether solution is washed with 200 ml of 20% hydrochloric acid and 200 ml of water, dried with sodium sulfate, filtered, and then evaporated to give 16.24 g (100%). This product is purified on a silica gel dry column (116 cm×5 cm, eluent=1:1 hexane-methylene chloride) by collecting a sample between 85 cm and 63 cm (solvent front=113 cm) to give 12.60 g (78%) of a clear slightly yellow colored oil.

Analysis calculated for $C_{26}H_{24}F_4O_4$: C, 65.54%; H, 5.08%; F, 15.95%. Found: C, 64.99%; H, 4.96%; F, 19.10%.

EXAMPLE 8

Preparation of α-Cyano-m-phenoxybenzyl, α-isopropyl-4-(1,1,2,2-tetrafluoroethoxy)phenylacetate To a stirred mixture of 8.81 g (7.49 g real, 0.0333 mol) of α-cyano-m-phenoxybenzyl alcohol, 3.0 ml (2.95 g, 0.0372 mol) of dried pyridine, and 20 ml of methylene chloride was added, over a period of 20 minutes, a 20 ml methylene chloride solution of 10.6 g (0.034 mol) of 3-methyl-2-[p-(1,1,2,2-tetrafluoroethoxy)phenyl]butyryl chloride. The reaction mixture is stirred at room temperature for 66 hours and then diluted with 200 ml of ether, washed with 200 ml of 20% hydrochloric acid and 200 ml of water, dried with sodium sulfate, filtered, and then evaporated to give a dark red oil. In order to remove the m-phenoxybenzaldehyde impurity the oil is reacted with 0.5 g of sodium borohydride at ice bath temperatures and the resulting oil is purified on a silica gel dry column (121 cm×5 cm, eluent=1:1 hexane-methylene chloride) by collecting a sample between 77 cm and 57 cm (solvent front=113 cm) to give 11.17 g (66%) of a clear orange oil.

Analysis calculated for $C_{27}H_{23}F_4NO_4$: C, 64.67%; H, 4.62%; N, 2.79%; F, 15.16%. Found: C, 65.26%; H, 4.81%; N, 2.82%; F, 17.94%.

EXAMPLE 9

Preparation of α-Isopropyl-4-methoxyphenylacetonitrile

A solution of sodium hydroxide (50%, 300 ml) is added to a solution of p-methoxyphenylacetonitrile (147 g, 1 mol), dicyclohexyl-18-crown-6 (18.63 g, 5 mol %), 2-bromopropane (320 g, 2.6 mol) and benzene (300 ml). The reaction mixture is heated to 45° C. and held for 4 days. The organic phase is separated, washed well with water (3×200 ml), dilute hydrochloric acid (1×200 ml), water (2×200 ml) and evaporated to an oil. Vacuum distillation gives the product (175.6 g, 81% real): boiling point 96° C. to 100° C. (0.15 mm); nmr (CDCl$_3$) shows that the distilled material contains 12.5 mol % of the starting nitrile.

EXAMPLE 10

Preparation of α-Isopropyl-4-hydroxyphenylacetonitrile

Boron tribromide (51.0 g, 0.2 mol) in methylene chloride (20 ml) is added to a solution of α-isopropyl-4-methoxyphenylacetonitrile (37.8 g, 0.2 mol) in methylene chloride (35 ml) maintained at −40° C. The red solution is allowed to warm to room temperature and stirred for 3 days. The reaction solution is added to ice, then extracted with ether (3×100 ml), washed with water (2×100 ml) and evaporated to an oil. Vacuum distillation gives the product: α-isopropyl-4-hydroxyphenylacetonitrile (28.9 g, 81%); boiling point 142° C. to 143° C. (0.25 mm).

EXAMPLE 11

Preparation of Formic acid, Chlorothio-, O-[p-(1-cyano-2-methylpropyl)phenyl]ester Thiophosgene (16.43 g, 0.143 mol) in chloroform (50 ml) is added over 30 minutes to a solution of α-isopropyl-4-hydroxyphenylacetonitrile (25.0 g, 0.143 mol) in NaOH solution (5%, 5.72 g, 0.143 mol), using an ice bath occasionally to maintain the temperature below 30° C. The mixture is stirred for 15 minutes and the chloroform layer is separated, washed with water and evaporated to a yellow oil (38.2 g). The product is used as such in Example 12.

EXAMPLE 12

Preparation of α-Isopropyl-4-trifluoromethoxyphenylacetonitrile

The thiocarbonate (38.2 g) from Example 11 is treated with molybdenum hexafluoride (15.8 g) at −25° C. The thick reaction mass is then allowed to warm to room temperature and then heated slowly to 160° C. using an oil bath. The mixture is cooled to room temperature and then poured into water and extracted with ether (4×50 ml), washed with water (1×50 ml) and evaporated to an oil. Vacuum distillation gives α-isopropyl-4-trifluoromethoxyphenylacetonitrile; boiling point 78° C. to 80° C. (0.15 mm).

EXAMPLE 13

Alternate Preparation of α-Isopropyl-4-trifluoromethoxyphenylacetonitrile

A. Preparation of 4-Trifluoromethoxybenzyl chloride

A mixture of trioxane (355 mg), zinc chloride (340 mg) and trifluoromethoxybenzene (600 mg) is heated at 73° C. while hydrogen chloride gas is bubbled through the reaction mixture. The reaction is cooled to room temperature and diluted with ether. The organic phase is washed with saturated sodium carbonate solution and water. Removal of the solvents gives the product as a colorless liquid (1.42 g).

B. Preparation of 4-Trifluoromethoxyphenylacetonitrile

The above chloro compound is converted to the corresponding nitrile by the procedure used in Example 3 in 93% yield.

C. Preparation of α-Isopropyl-4-trifluoromethoxyphenylacetonitrile

The alkylation of 4-trifluoromethoxyphenylacetonitrile is carried out in 90% yield by the procedure illustrated in Example 4.

EXAMPLE 14

Preparation of α-Isopropyl-4-trifluoromethoxyphenylacetic acid

A mixture of α-isopropyl-4-trifluoromethoxyphenylacetonitrile (2.0 g), potassium hydroxide (3.0 g) in ethylene glycol (35 ml) and water (3 ml) is heated at 140° C. for 8 hours. The solution is poured into water and extracted with ether (2×10 ml). The aqueous layer is acidified with dilute hydrochloric acid and extracted with ether (3×10 ml), washed with water (1×25 ml), dried (Na$_2$SO$_4$) and evaporated to an oil (1.23 g); ir (neat) 1700 cm$^{-1}$.

EXAMPLE 15

Preparation of α-Isopropyl-4-trifluoromethoxyphenylacetyl chloride

A solution of α-isopropyl-4-trifluoromethoxyphenylacetic acid (1.2 g) and thionyl chloride (0.6 ml) in benzene (5 ml) is refluxed for 4 hours. Evaporation of the solvent and excess thionyl chloride gives the acid chloride which is used as such for esterification in Examples 16 and 17.

EXAMPLE 16

Preparation of α-Cyano-m-phenoxybenzyl α-isopropyl-4-trifluoromethoxyphenylacetate A solution of α-isopropyl-4-trifluoromethoxyphenylacetyl chloride (4.58 mmol) in ether (5 ml) is added to an ether (20 ml) solution of α-cyano-m-phenoxybenzyl alcohol (4.58 mmol) and pyridine (0.5 ml). The mixture is stirred overnight and filtered. The filtrate and the washings are evaporated and the residual oil is purified on 5×2 mm silica gel plates using 1:1 methylenechloride-hexane as eluent. The band with Rf=0.55 is extracted with ether and evaporated to give the desired ester (0.85 g).

IR (neat) 1755 cm$^{-1}$; nmr (CDCl$_3$) δ 6.8–7.6 (m, 13H, ArH), 6.31 and 6.28

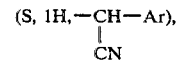

(S, 1H, —CH—Ar),
|
CN 3.27 [d, J=7 Hz, 1H, CH—CH(CH$_3$)$_2$], 2.0–2.6 [m, 1H, CH(CH$_3$)$_2$], 0.6–1.2 (four doublets, J=7 Hz, 6H, isopropyl CH$_3$); $^{19}$F chemical shift 58.8 δ relative to CFCl$_3$.

EXAMPLE 17

Preparation of m-Phenoxybenzyl α-isopropyl-4-trifluoromethoxyphenylacetate

To a solution of m-phenoxybenzyl alcohol (1.89 g) and pyridine (1 ml) in methylene chloride (6 ml) is added a methylene chloride (7 ml) solution of α-isopropyl-4-trifluoromethoxyphenylacetyl chloride, prepared from the corresponding acid (2.46 g) as illustrated in Example 15. After stirring the reaction mixture overnight, it is washed with water, dilute hydrochloric acid solution, dilute potassium hydroxide solution, water and evaporated to an orange oil. Purification by silica gel chromatography gives the desired ester (2.76 g).

IR (neat) 1738 cm$^{-1}$; nmr (CDCl$_3$) δ 6.73-7.45 (m, 13H), 5.03 (S, 2H), 3.20 (d, J=10.5 Hz, 1H), 2.26 (m, 1H), 0.66 and 0.94 (two d, J=6.6 Hz, 6H).

EXAMPLE 18

Prparation of α-Ethyl- and α-n-propyl-4-trifluoromethoxyphenylacetic acids and esters thereof Following the procedure of Example 9, but substituting ethyl bromide and 1-bromopropane for 2-bromopropane and proceeding with the steps exemplified by Examples 10, 11, 12 and 14, afforded the acids, α-ethyl-4-trifluoromethoxyphenylacetic and α-n-propyl-4-trifluoromethoxyphenylacetic acids, respectively. These acids were then converted into the following esters by the appropriate procedures of Examples 15, 16 and 17.

$$CF_3O-\underset{R_1}{\underset{|}{C_6H_4}}-\underset{}{CH}-\overset{O}{\underset{\|}{C}}-O-\underset{R_2}{\underset{|}{CH}}-C_6H_4-O-C_6H_5$$

| R$_1$ | R$_2$ | NMR Assignments |
|---|---|---|
| C$_2$H$_5$ | H | δ0.83 (t, J = 7.5Hz, 3H, CH$_3$), 1.90 (m, 2H, —CH$_2$—), 3.49 (t, J = 7.5Hz, —CH—CH$_2$CH$_3$), 5.04 (s, 2H, —OCH$_2$—), 7.10 (m, 13H, ArH) |
| C$_2$H$_5$ | CN | δ0.84 (two triplets, J = 7.6Hz, 3H, CH$_3$), 1.94 (m, 2H, —CH$_2$—), 3.55 (t, J = 7.4Hz, 1H, —CHCH$_2$CH$_3$), 6.33 (s, 1H, —CHCN—), 7.18 (m, 13H, ArH) |
| n-C$_3$H$_7$ | H | δ0.6-2.4 (m, 7H, —CH$_2$CH$_2$CH$_3$), 3.63 (t, J = 7.2Hz, 1H, —CH—C$_3$H$_7$), 7.12 (m, 13H, ArH) |
| n-C$_3$H$_7$ | CN | δ0.65-2.4 (m, 7H, —CH$_2$CH$_2$CH$_3$), 3.71 (t, J = 7.3Hz, 1H, —CH—C$_3$H$_7$), 7.20 (m, 13H, ArH) |

EXAMPLE 19

Preparation of α-Bromo-4-trifluoromethylthiotoluene

Bromine (20.5 g, 0.13 mol) in 20 ml of carbon tetrachloride is added slowly to a solution of 4-trifluoromethylthiotoluene (29 g, 0.15 mol) in 90 ml of carbon tetrachloride heated to gentle reflux under a 275 W sunlamp. When the addition is complete, the solution is maintained at reflux for one hour. Most of the solvent is removed at atmospheric pressure, then the residue is vacuum distilled. The 15.5 g cut with boiling point 64°-77° C./0.6-0.8 mm is 92% monobromo compound by glc.

EXAMPLE 20

Preparation of 4-Trifluoromethylthiophenylacetonitrile

Sodium cyanide (3.9 g, 0.08 mol) is added to 40 ml of dimethylsulfoxide at 65° C. under N$_2$. The heat is removed and α-bromo-4-trifluoromethylthiotoluene (14.3 g real, 0.053 mol) is added dropwise at such a rate that the exotherm never raises the temperature above 75° C. The red-colored reaction is heated to 90°-95° C. for about 45 minutes, then cooled to room temperature and treated with 50-100 ml of ice water. The aqueous suspension is extracted with several portions of ether which are combined, washed with water, and dried over sodium sulfate. Evaporation in vacuo gives 9.7 g of a dark red oil 95% pure by glc.

EXAMPLE 21

Preparation of α-Isopropyl-4-trifluoromethylthiophenylacetonitrile

Fifty percent sodium hydroxide (13.5 ml) is added over a 30-minute period dropwise to a suspension of 4-trifluoromethylthiophenylacetonitrile (9.7 g, 0.045 mol), 2-iodopropane (9.5 g, 0.056 mol), and 18-crown-6 (0.61 g, 0.0023 mol) in 13.5 ml of benzene and the exotherm reaches 43° C. After stirring 2.5 hours at ambient temperature, an aliquot placed on glc shows none of the starting nitrile remaining. The reaction is worked up by adding ice water and extracting with ether, which is washed with 10% HCl, water, and dried over sodium sulfate. Evaporation in vacuo gave 10.2 (86.8%) of a red-brown oil.

Comparable results are obtained substituting ethyl bromide or n-propyliodide in place of 2-iodopropane to synthesize α-ethyl-4-trifluoromethylthiophenylacetonitrile and α-n-propyl-4-trifluoromethylthiophenylacetonitrile, respectively.

EXAMPLE 22

Preparation of α-Isopropyl-4-trifluoromethylthiophenylacetic acid

α-Isopropyl-4-trifluoromethylthiophenylacetonitrile (6.9 g real, 0.0265 mol) and 50% sodium hydroxide (25 g, 0.312 mol) are combined in 53 ml of ethylene glycol and heated at gentle reflux for 18 hours. The reaction is poured into ice water and extracted with ether. The aqueous phase is acidified with concentrated HCl, then re-extracted with ether which is washed with water and dried over sodium sulfate. Evaporation in vacuo gives 2.05 g of an oily product.

Comparable results are obtained substituting α-ethyl-4-trifluoromethylthiophenylacetonitrile or α-n-propyl-4-trifluoromethylthiophenylacetontrile, as the starting material to synthesize α-ethyl-4-trifluoromethylthiophenylacetic acid and α-n-propyl-4-trifluoromethylthiophenylacetic acid, respectively.

EXAMPLE 23

Preparation of α-Cyano-m-phenoxybenzyl α-isopropyl-4-trifluoromethylthiophenylacetate By using α-isopropyl-4-trifluoromethylthiophenylacetic acid and procedures of Examples 15 and 16, the product is obtained as an oil.

Analysis calculated for $C_{26}H_{22}F_3NO_3S$: C, 64.32%; H, 4.57%; F, 11.74%; N, 2.89%; S, 6.60%. Found: C, 64.27%; H, 4.62%; F, 11.66%; N, 2.68%; S, 6.43%.

Comparable results are obtained substituting α-ethyl-4-trifluoromethylthiophenylacetic acid or α-n-propyl-4-trifluoromethylthiophenylacetic acid to synthesize α-cyano-m-phenoxybenzyl α-ethyl-4-trifluoromethylthiophenylacetate and α-cyano-m-phenoxybenzyl α-n-propyl-4-trifluoromethylthiophenylacetate, respectively.

EXAMPLE 24

Preparation of m-Phenoxybenzyl α-isopropyl-4-trifluoromethylthiophenylacetate

By using α-isopropyl-4-trifluoromethylthiophenylacetic acid and procedures of Examples 15 and 17, the product is obtained as an oil.

EXAMPLE 25

Preparation of α-Isopropyl-4-mercaptophenylacetic acid

A solution of α-isopropyl-4-difluoromethylthiophenylacetonitrile (15.7 g, 0.065 mol) in sodium hydroxide solution (50%, 42 g) and ethylene glycol (80 ml) is heated at reflux for 18 hours. The reaction mixture is poured into ice water and extracted with ether. The alkaline layer is acidified at 15°-20° C. using concentrated hydrochloric acid and extracted with ether. The ether extract is washed with water, saturated sodium chloride solution and evaporated to give an oil (11.4 g, 83%). NMR and ir indicate that the —$CHF_2$ radical has been removed during the reaction and the product is the thiol.

EXAMPLE 26

Preparation of α-Isopropyl-4-difluoromethylthiophenylacetic acid

Sodium hydroxide (18.4 g, 0.46 mol) in 50 ml of water and α-isopropyl-4-mercaptophenylacetic acid (11 g, 0.05 mol) in 40 ml of dioxane are combined and heated to a temperature of 50° C. Chlorodifluoromethane (Freon-22) is bubbled in slowly under the surface of the liquid causing an immediate exotherm to 75° C. The addition is continued until the exotherm slowly begins to subside (about 0.5 hour). The reaction is cooled to room temperature and treated with 100 ml of ice water. The aqueous layer is extracted with 3×200 ml of ether, then acidified at 15°-20° C. with concentrated HCl. The resulting oil is removed by ether extraction. The ether solution is washed with water and saturated sodium chloride before drying over sodium sulfate and evaporation in vacuo to give 10.2 g of a dark brown gum. This is used without further purification in the final esterification step.

Following the above procedure, but substituting α-isopropyl-3-chloro-4-mercaptophenylacetic acid for α-isopropyl-4-mercaptophenylacetic acid in the procedure, yields α-isopropyl-3-chloro-4-difluoromethylthiophenylacetic acid.

EXAMPLE 27

Preparation of α-Cyano-m-phenoxybenzyl α-isopropyl-4-difluoromethylthiophenylacetate By using α-isopropyl-4-difluoromethylthiophenylacetic acid and procedures of Examples 15 and 16, the product was obtained as an oil.

Analysis calculated for $C_{26}H_{23}F_2NO_3S$: C, 66.79%; H, 4.96%; F, 8.13%; N, 3.00%; S, 6.86%. Found: C, 66.58%; H, 5.13%; F, 8.02%; N, 2.87%; S, 6.95%.

EXAMPLE 28

Preparation of α-Isopropyl-4-hydroxyphenylacetic acid

A mixture of α-isopropyl-4-methoxyphenylacetonitrile (40.0 g) and hydrobromic acid (48%, 200 ml) is refluxed at 126°-128° C. using an oil bath for 14 hours. The reaction mixture is diluted with ice and water, extracted several times with ether, washed with water and evaporated to a solid residue. The solid is boiled with chloroform (200 ml), cooled, filtered and dried: yield, 23.8 g; melting point 172°-174° C.; ir (Nujol) 3250-2900 (broad, OH), 1690 cm$^{-1}$ (C=O).

Comparable results are obtained substituting α-ethyl-4-methoxyphenylacetontrile or α-n-propyl-4-methoxyphenylacetonitrile to synthesize α-ethyl-4-hydroxyphenylacetic acid and α-n-propyl-4-hydroxyphenylacetic acid, respectively.

EXAMPLE 29

Preparation of α-Isopropyl-4-difluoromethoxyphenylacetic acid

Into an 80° C. magnetically stirred mixture of 10.00 g (0.0515 mol) of α-isopropyl-4-hydroxyphenylacetic acid, 65 ml of dioxane, 19.08 g (18.56 g real, 0.464 mol) of sodium hydroxide, and 30 ml of water is bubbled 46 g (0.532 mol) of chlorodifluoromethane over a period of 4 hours. The reaction mixture is poured into 250 ml of ice water and the resulting mixture is washed with ether, acidified with concentrated hydrochloric acid to pH 3, and then extracted with 200 ml of ether. The ether solution is washed once with 100 ml of water, dried with sodium sulfate, filtered, and then evaporated to give a white paste. A mixture of hexane and methylene chloride is added and the resulting mixture is filtered to remove the solid which is the starting material. The filtrate is evaporated to give 5.41 g of a clear brown oil. It is estimated that the product was at least 85% pure by nmr. NMR (CDCl$_3$-d$_5$ pyridine), δ 7.43 (d, J=8.2 Hz, 2H), δ 7.08 (d, J=8.2 Hz, 2H), δ 6.57 (t, J=74.3 Hz, 1H), δ 3.63 (s, imp.), δ 3.25 (d, J=10 Hz, 1H), δ 2.37 (m, 1H), δ 1.19 (d, J=6.5 Hz, 3H), δ 0.78 (d, J=6.5 Hz, 3H), δ 13.82 (s, 1H).

Comparable results are obtained substituting α-ethyl-4-hydroxyphenylacetic acid or α-n-propyl-4-hydroxyphenylacetic acid to synthesize α-ethyl-4-difluoromethoxyphenylacetic acid and α-n-propyl-4-difluoromethoxyphenylacetic acid, respectively.

EXAMPLE 30

Preparation of m-Phenoxybenzyl α-isopropyl-4-difluoromethoxyphenylacetate

By using α-isopropyl-4-difluoromethoxyphenylacetic acid and procedures of Examples 15 and 17, the product was obtained as a pale yellow oil.

Analysis calculated for $C_{25}H_{24}F_2O_4$: C, 70.41%; H, 5.67%; F, 8.91%. Found: C, 73.36%; H, 5.96%; F, 10.56%.

Comparable results are obtained substituting α-ethyl-4-difluoromethoxyphenylacetic acid or α-n-propyl-4-difluoromethoxyphenylacetic acid to synthesize m-phenoxybenzyl α-ethyl-4-difluoromethoxyphenylacetate or α-n-propyl-4-difluoromethoxyphenylacetate, respectively.

EXAMPLE 31

Preparation of α-Cyano-m-phenoxybenzyl α-isopropyl-4-difluoromethoxyphenylacetate By using α-isoproppyl-4-difluoromethoxyphenylacetic acid and procedures of Examples 15 and 16, the product was obtained as an oil.

NMR (CDCl$_3$) δ 0.88 (four doublets, J=6 Hz, 6H, CH$_3$), 2.30

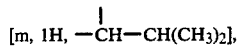

[m, 1H, —CH—CH(CH$_3$)$_2$], 3.24 [d, J=10.1 Hz, 1H,

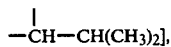

—CH—CH(CH$_3$)$_2$], 6.33

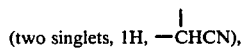

(two singlets, 1H, —CHCN), 6.45 (t, J=74 Hz, 1H, CHF$_2$O—), 7.16 (m, 13H, ArH).

Analysis calculated for $C_{26}H_{23}F_2NO_4$: C, 69.17%; H, 5.13%; F, 8.42%; N, 3.10%. Found: C, 69.41%; H, 5.20%; F, 10.25%; N, 3.70%.

Comparable results are obtained by substituting α-ethyl-4-difluoromethoxyphenylacetic acid or α-n-propyl-4-difluoromethoxyphenylacetic acid to synthesize α-cyano-m-phenoxybenzyl α-ethyl-4-difluoromethoxyphenylacetate and α-cyano-m-phenoxybenzyl α-n-propyl-4-difluoromethoxyphenylacetate, respectively.

EXAMPLE 32

Preparation of m-Phenoxybenzyl α-isopropyl-4-trifluoromethylsulfinylphenylate

A mixture of 10.0 g of m-phenoxybenzyl α-isopropyl-4-trifluoromethylthiophenylacetate of Example 24, and 4.1 g of m-chloroperbenzoic acid (85%) are warmed in 100 ml of methylene chloride for several hours. The mixture is filtered and the concentrated residue is purified on a silica gel dry column using a 2:1 methylene chloride-hexane mixture. The product is collected as a pale yellow oil.

Comparable results are obtained substituting m-phenoxybenzyl α-ethyl-4-trifluoromethylthiophenylacetate or m-phenoxybenzyl α-n-propyl-4-trifluoromethylthiophenylacetate to synthesize m-phenoxybenzyl α-ethyl-4-trifluoromethylsulfinylphenylacetate and m-phenoxybenzyl α-n-propyl-4-trifluoromethylsulfinylphenylacetate, respectively.

EXAMPLE 33

Preparation of α-Cyano-m-phenoxybenzyl α-ethyl-3-difluoromethylsulfonylphenylacetate A mixture of 10.0 g of α-cyano-m-phenoxybenzyl α-ethyl-3-difluoromethylthiophenylacetate and 9.0 g of m-chloroperbenzoic acid (85%) are refluxed in 100 ml of ethylene dichloride overnight. The mixture, after filtering and concentrating, is purified by dry column chromatography on silica gel using a 2:1 methylene chloride-hexane mixture. The product is collected as a yellow oil.

Comparable results are obtained by substituting α-cyano-m-phenoxybenzyl α-isopropyl-4-trifluoromethylthiophenylacetate or α-cyano-m-phenoxybenzyl α-n-propyl-4-trifluoromethylthiophenylacetate to synthesize α-cyano-m-phenoxybenzyl α-isopropyl-4-trifluoromethylsulfonylphenylacetate and α-cyano-m-phenoxybenzyl α-n-propyl-4-trifluoromethylsulfonylphenylacetate, respectively.

EXAMPLE 34

Preparation of 4-Trifluoromethoxy-β,β-dimethylatropic acid

To a solution of p-trifluoromethoxyphenylacetic acid (22 g, 0.1 mol, obtained by alkaline hydrolysis of the nitrile prepared in Example 12) in ether (50 ml) is added at ice bath temperature, commercially available isopropyl magnesium chloride solution (0.2 mol) in ether. The reaction mixture is stirred for 2 hours at room temperature and dry acetone (5.8 g, 0.1 mol) is added to the reaction mixture and refluxed for 5 hours. The reaction mixture is cooled, cautiously acidified with aqueous sulfuric acid and extracted with ether. Combined organic layers are extracted with 10% sodium carbonate solution. The alkaline layer is acidified with hydrochloric acid and extracted with ether. The ether extract is dried (Na$_2$SO$_4$) and evaporated to give 4-trifluoromethoxy-β,β-dimethylatropic acid.

EXAMPLE 35

Preparation of m-Phenoxybenzyl 4-trifluoromethoxy-α-isopropenylphenylacetate

To a solution of 4-trifluoromethoxy-β,β-dimethylatropic acid (13.9 g, 0.05 mol) and triethylamine (6.1 g, 0.06 mol) in acetone (100 ml) is added m-phenoxybenzylbromide (13.2 g, 0.05 mol) at ice bath temperature and then refluxed for 4 hours. The mixture is poured into cold dilute hydrochloric acid and extracted with ether. The ether layer is washed with 10% hydrochloric acid, water, dried (Na$_2$SO$_4$) and evaporated to give the hydroxy ester which is dehydrated with P$_2$O$_5$ in benzene at 80° C. for 18 hours. Filtration and removal of the solvent gives the crude ester. Purification of the material by dry column chromatography with silica gel using 50:50 methylene chloride-hexanes as solvent gives the product as pale yellow gum.

EXAMPLE 36

Preparation of 4-Trifluoromethoxy-α-t-butylbenzyl alcohol

To a solution of commercially available t-butyl magnesium chloride in THF (1.0 mol) is added at 38°–40° C. a solution of 4-trifluoromethoxybenzaldehyde (56 g, 0.4 mol) in THF (50 ml) under nitrogen atmosphere. The reaction solution is stirred at room temperature overnight and cautiously acidified with dilute sulfuric acid at 15°-20° C. Ether is added and the organic phase is washed with water, dried (Na$_2$SO$_4$) and evaporated to a gummy solid. The crude material is purified by silica gel chromatography to give the alcohol which is used in Example 37.

EXAMPLE 37

Preparation of p-(1-Chloro-2,2-dimethylpropyl)-α,α,α-trifluoroanisole

To freshly distilled thionyl chloride (14.87 g, 0.125 mol) cooled in salt ice bath is added in portions the neopentyl alcohol of Example 36 (12.4 g, 0.05 mol) over 30 minutes. The ice bath is removed and the slurry is left to stand overnight. Evaporation of excess thionyl chloride gives a solid.

EXAMPLE 38

Preparation of α-t-Butyl-4-trifluoromethoxyphenylacetic acid

The neopentyl chloride prepared in Example 37 is converted to the Grignard reagent and subsequent carbonation with carbon dioxide according to the procedure of Weinstein and Morse [Journal of the American Chemical Society 74, 1133 (1952)] gives the desired acid as a white solid.

EXAMPLE 39

Preparation of α-Cyano-m-phenoxybenzyl α-t-butyl-4-trifluoromethoxyphenylacetate By using α-t-butyl-4-trifluoromethoxyphenylacetic acid and using procedures of Examples 15 and 16, the product is obtained as an oil.

EXAMPLE 40

Preparation of α-Isopropyl-3-bromo-4-hydroxyphenylacetic acid

A mixture of α-isopropyl-4-hydroxyphenylacetic acid (20 g, 0.103 mol) in chloroform (250 ml) is cooled to 0° C. and bromine (16.5 g, 0.103 mol) in chloroform (15 ml) is added over 30 minutes. The reaction solution is stirred at 0° C. for 30 minutes and then allowed to warm to room temperature. The solvent is evaporated and the residue is crystallized from hexanes-benzene to give the monobromo derivative (22.1 g); melting point 113° C. to 116° C.

EXAMPLE 41

Preparation of α-Isopropyl-3-bromo-4-difluoromethoxyphenylacetic acid

Using the procedure described in Example 29, α-isopropyl-3-bromo-4-hydroxyphenylacetic acid (18.0 g) is converted to the corresponding difluoromethoxy acid. The desired acid is obtained by separation of the unreacted starting material by chromatography on silica gel using 2.5% methanol in chloroform as eluent as a waxy solid (4.7 g). This crude acid is used as such in Example 42 and 43.

EXAMPLE 42

Preparation of m-Phenoxybenzyl α-isopropyl-3-bromo-4-difluoromethoxyphenylacetate By using α-isopropyl-3-bromo-4-difluoromethoxyphenylacetic acid and procedures of Examples 15 and 17, the product is obtained as a pale yellow gum. NMR (CDCl$_3$), δ 6.8-7.7 (m, 12H, ArH), 6.45 (t, J=74 Hz, 1H, OCHF$_2$), 5.10 (bs, 1H, CH$_2$) 3.18 (d, J=9 Hz, 1H, C$\underline{\text{H}}$—CH(CH$_3$)$_2$), 1.0 and 0.71 (2d, J=6 Hz, 6H, isopropyl CH$_3$).

EXAMPLE 43

Preparation of α-Cyano-m-phenoxybenzyl α-isopropyl-3-bromo-4-difluoromethoxyphenylacetate By using α-isopropyl-3-bromo-4-difluoromethoxyphenylacetic acid and procedures of Examples 15 and 16, the product is obtained as a yellow gum. NMR (CDCl$_3$) δ 6.9-7.7 (m, 12H, ARH), 6.50 (t, J=74Hz, 1H, OCHF$_2$) 6.33 and 6.36 (2S, 1H, C$\underline{\text{H}}$—CN), 3.25 (d, 1H, C$\underline{\text{H}}$—CH(CH$_3$)), 0.6-1.1 (4d, 6H, isopropyl CH$_3$).

EXAMPLE 44

Preparation of α-Isopropyl-3-chloro-4-hydroxyphenylacetic acid

A mixture of α-isopropyl-4-hydroxyphenylacetic acid (30 g, 0.154 mol) in chloroform (600 ml) is cooled to 0° to 5° C. and chlorine gas (12.0 g, 0.169 mol) is bubbled slowly. The solvent is removed and the product is obtained by crystallization from benzene-hexanes: m.p. 125°–128° C.

EXAMPLE 45

Preparation of α-cyano-m-phenoxybenzyl α-isopropyl-3-chloro-4-difluoromethoxyphenylacetate By using α-isopropyl-3-chloro-4-hydroxyphenylacetic acid and procedures of Examples 29, 15, and 16, the product is obtained as a gum. NMR (CDCl$_3$) δ 6.8 to 7.5 (m, 12H, ArH), 6.50 (t, J=74 Hz, 1H, OCHF$_2$), 6.33 and 6.30 (2H, 1H, —CH—CN), 3.25 (d, J=10 Hz, 1H, C$\underline{\text{H}}$—CH(CH$_3$)$_2$).

Analysis calculated for C$_{26}$H$_{22}$ClF$_2$NO$_4$: C 64.26; H 4.56; N, 2.88; Cl 7.30; F 7.82; Found: C 64.27; H 4.70; N 2.94; Cl 7.20; F 7.78.

EXAMPLE 46

Preparation of m-Phenoxybenzyl α-isopropyl-3-chloro-4-difluoromethoxyphenylacetate By using α-isopropyl-3-chloro-4-hydroxyphenylacetic acid and procedures of Examples 29, 15 and 17, the product is obtained as a yellow oil. NMR (CDCl$_2$) δ 6.8 to 7.6 (m, 12H, ArH), 6.47 (t, J=74 Hz, OCHF$_2$), 5.07 (bs, 2H, CH$_2$).

Analysis calculated for C$_{25}$H$_{23}$ClF$_2$O$_4$: C 65.15; H 5.03; Cl 7.69; F 8.24; Found: C 65.46; H 5.05; Cl 7.73; F 8.08.

EXAMPLE 47

Preparation of α-Isopropyl-3,5-dichloro-4-hydroxyphenylacetic acid.

A mixture of α-isopropyl-4-hydroxyphenylacetic acid (30 g, 0.155 mol) is chloroform (500 ml) is chilled in ice-salt bath and chlorine gas (ca 30-35 g) is bubbled at 0° to 5° C. for 90 minutes. The solution is stirred at 0° to 5° C. for an additional hour and allowed to warm to room temperature. The solvent is evaporated and the product is obtained by crystallization from hexanes as a white solid (29.8 g); m.p. 152°-154°.

EXAMPLE 48

Preparation of
α-Isopropyl-3,5-dichloro-4-difluoromethoxyphenylacetic acid

By using α-isopropyl-3,5-dichloro-4-hydroxyphenylacetic acid and procedure of Example 29, the above acid is obtained as an oil. The nmr of the product indicates that it contains 15 mole percent (approx.) of the starting material, and is used as such in Example 49.

EXAMPLE 49

Preparation of α-Cyano-m-phenoxybenzyl α-isopropyl-3-bromo-4-difluoromethoxyphenylacetate By using α-isopropyl-3,5-dichloro-4-difluoromethoxyphenylacetic acid and procedures of Examples 15 and 16, the product is obtained as a yellow gum, NMR (CDCl$_3$) δ 6.9–7.7 (m, 11H, ArH), 6.67 (t, J=74 Hz, 1H, OCHF$_2$), 6.33 and 6.40 (2S, 1H, C$\underline{H}$—CN), 3.23 (d, J=10 Hz, 1H, CH—C$\underline{H}$(CH$_3$)$_2$, 0.6 to 1.1 (4d, 6H, isopropyl CH$_3$).

Analysis calculated for C$_{22}$H$_2$Cl$_2$F$_2$NO$_4$: C 60.01; H 4.07; N 2.69; Found: C 59.78; H 4.30; N 2.31.

EXAMPLE 50

Preparation of m-Phenoxybenzyl α-isopropyl-3,5-dichloro-4-difluoromethoxyphenylacetate By using α-isopropyl-3,5-dichloro-4-difluoromethoxyphenylacetic acid and procedures of Examples 15 and 17, the product is obtained as a gum.

Analysis calculated for C$_{25}$H$_{22}$Cl$_2$F$_2$O$_4$: C 60.61; H 4.48; Cl 14.32; F 7.67; Found: C 60.50; H 4.60; Cl, 14.13; F 7.52.

EXAMPLE 51

Preparation of
α-Isopropyl-3-methyl-4-difluoromethoxyphenylacetic acid

3-Methyl-4-methoxyphenylacetonitrile is converted to the above compound using procedures of Examples 28 and 29. The product is contaminated into some α-isopropyl-3-methyl-4-hydroxyphenylacetic acid as indicated by nmr. However, the material is used as such for esterification in Example 52 where the final ester is purified by chromatography.

EXAMPLE 52

Preparation of α-cyano-m-phenoxybenzyl α-isopropyl-3-methyl-4-difluoromethoxyphenylacetate Using the acid obtained in Example 51 and the procedures of Examples 15 and 16, the ester is obtained as a viscous oil. NMR (CDCl$_3$) δ 6.8–7.6 (m, 12H, ArH), 6.45 (t, J=74 Hz, 1H, OCHF$_2$), 6.48 and 6.53 (2S, 1H, CH—CN), 2.25 (S, 3H, CH$_3$).

Analysis calculated for C$_{27}$H$_{25}$F$_2$NO$_4$: C 69.66; H 5.41; N 3.01; Found: C 70.05; H 5.86; N 2.83.

EXAMPLE 53

Preparation of 3-Fluoro-4-methoxyphenylacetonitrile

A mixture of 4-(bromomethyl)-2-fluoroanisole (45.8 g, 0.21 mol), trihexylamine (1.4 g) and sodium cyanide (20.5 g, 0.42 mol) in water (50 ml) is heated at 60°–65° C. for 18 hours. The mixture is cooled and extracted in its ether, washed with water, saturated sodium chloride solution and dried (CNa$_2$SO$_4$). Evaporation of the solvent gives a solid, (33.2 g): m.p. 42°–46° C.

EXAMPLE 54

Preparation of
α-Isopropyl-3-fluoro-4-methoxyphenylacetonitrile

A mixture of 3-fluoro-4-methoxyphenylacetonitrile (30 g, 0.18 mol), 2-bromopropane (27.7 g, 0.225 mol), benzyltriethylammonium chloride (2.3 g, 0.01 mol) and sodium hydroxide solution (50%, 66 ml) is heated at 55° for 1 hour and cooled. The mixture is diluted with water, extracted with ether, washed with water, 1 NHCl, water, and dried (Na$_2$SO$_4$). Evaporation gives the product as a brown oil (30.7 g). NMR spectrum shows the benzylic proton as a doublet at 3.6 δ.

EXAMPLE 55

Preparation of
α-Isopropyl-3-fluoro-4-difluoromethoxyphenylacetic acid

Starting with α-isopropyl-3-fluoro-4-methoxyphenylacetonitrile and following the procedures of Examples 28 and 29, the product is obtained as a brown oil. NMR spectrum shows that the product is contaminated with the starting material. Hence this crude reaction mixture is subjected to the Freon 22 reaction two more times as described in Example 29 to give the product as a brown oil. NMR spectrum indicates that the product is approximately 96% by weight.

EXAMPLE 56

Preparation of α-cyano-m-phenoxybenzyl α-isopropyl-3-fluoro-4-difluoromethoxyphenylacetate Starting with α-isopropyl-3-fluoro-4-difluoromethoxyphenylacetic acid and following the procedures of Examples 15 and 16, the final ester is prepared as yellow oil. NMR (CDCl$_3$) δ 6.8 to 7.5 (m, 12H, ArH), 6.63 (t, J=74 Hz, 1H, OCHF$_2$), 6.33 and 6.37 (2S, 1H, CH—CN).

Analysis calculated for C$_{26}$H$_{22}$F$_3$NO$_4$: C 66.52; H 4.72; N 2.98; Found: C 66.27; H 4.87; N 2.99.

EXAMPLE 57

Preparation of
α-Isopropyl-3-nitro-4-hydroxyphenylacetic acid

A mixture of α-isopropyl-4-hydroxyphenylacetic acid (18.2 g, 0.094 mol) in acetic acid (130 ml) is heated to 40° C. and nitric acid (70%, 9.56 g, 0.095 mol) is added at such a rate that the reaction temperature is maintained at 38°–40° and never exceeded 45° C. The reaction mixture is stirred at 40°–42° C. overnight and poured into ice-water. The yellow solid is collected by filtration, washed and dried (19.1 g); m.p. 103°–105°.

EXAMPLE 58

Preparation of
α-Isopropyl-3-nitro-4-difluoromethoxyphenylacetic acid

Using α-isopropyl-3-nitro-4-hydroxyphenylacetic acid and procedure of Example 29, the above acid is prepared as a crude material containing unreacted starting material. However, repeating of the Freon 22 reaction as described in Example 29 three times using the crude product obtained after each cycle, the product is finally obtained as a fine beige solid (hexanes): m.p. 88°–90°.

EXAMPLE 59

Preparation of α-Cyano-m-phenoxybenzyl α-isopropyl-3-nitro-4-difluoromethoxyphenylacetate Using α-isopropyl-3-nitro-4-difluoromethoxyphenylacetic acid and procedures of Examples 15 and 16, the product is obtained as a yellow oil.

Analysis calculated for $C_{26}H_{22}F_2N_2O_6$: C 62.90; H 4.47; N 5.64; Found: C 62.51; H 4.77; N 5.58.

EXAMPLE 60

Preparation of α-Cyano-m-phenoxybenzyl α-isopropyl-3-methoxy-4-difluoromethoxyphenylacetate Using α-isopropyl-3-methoxy-4-difluoromethoxyphenylacetic acid and procedures of Examples 15 and 16, the product can be prepared as a gum.

EXAMPLE 61 most of the pyridine is removed by distillation and the reaction is cooled and diluted into toluene (80 ml). The solids are filtered and the filtrate is washed with 20% HCl, water, 5% NaOH, and water, respectively and evaporated to a dark brown oil. Vac Distillation gives the product as a clear liquid (6.6 g): b.p. 82°–88° C. (0.5 mm).

Analysis calculated for $C_{13}H_9FO_2$: C 72.22; H 4.20; F 8.79; Found: C 72.03; H 4.30; F 8.60.

EXAMPLE 62

Preparation of substituted α-Cyano-m-phenoxybenzyl esters of fluoroalkoxyphenylacetic acids Starting with either α-isopropyl-4-difluoromethoxyphenylacetic acid or α-isopropyl-4-trifluoromethoxyphenylacetic acid and the cyanohydrin of an appropriately substituted aldehyde, and using procedures of Examples 15 and 16, the following esters are prepared:

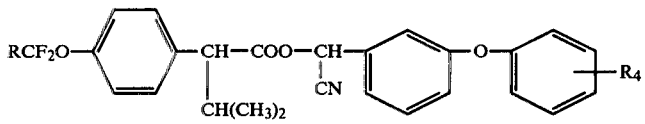

| R | R4 | NMR Assignments | Analysis Calculated | Analysis found |
|---|---|---|---|---|
| H | p-Cl | δ 6.8 to 7.5 (m, 12H, ArH), | C 64.27 | C 64.54 |
| | | 6.45 (t, J = 74Hz, 1H, OCHF2), | H 4.56 | H 4.92 |
| | | 6.30, 6.33 (2S, 1H, CH—CN), | N 2.88 | N 2.82 |
| | | 3.25 (d, J = 10Hz, 1H, CH—CH(CH3)2), | | |
| | | 0.6 to 1.2 (d, 6H, isopropyl CH3) | | |
| H | p-OCH3 | 6.8 to 7.4 (m, 12H, ArH) | C 67.35 | C 67.30 |
| | | 6.47 (t, J = 74Hz, 1H, OCHF2), | H 5.23 | H 5.46 |
| | | 6.28, 6.33 (2S, 1H, CN—CN), | N 2.91 | N 2.92 |
| | | 3.80 (S, 3H, OCH3) | | |
| H | p-CH3 | 6.8 to 7.5 (m, 12H, ArH), | C 69.67 | C 69.37 |
| | | 6.50 (t, J = 74Hz, 1H, OCHF2), | H 5.41 | H 5.72 |
| | | 6.33, 6.37 (2S, 1H, CH—CN), | N 3.01 | N 2.82 |
| | | 2.40 (S, 3H, CH3) | | |
| H | p-F | 6.8 to 7.5 (m, 12H, ArH), | C 66.51 | C 66.48 |
| | | 6.47 (t, J = 74Hz, 1H, OCHF2), | H 4.73 | H 4.95 |
| | | 6.30, 6.36 (2S, 1H, —CH—CN), | N 2.98 | N 2.64 |
| F | p-F | 6.8 to 7.5 (m, 12H, ArH) | C 64.06 | C 63.85 |
| | | 6.32, 6.37 (2S, 1H, —CH—CN), | H 4.35 | H 4.31 |
| | | 3.30 (d, J = 10Hz, 1H, CH—CH(CH3)2) | N 2.87 | N 2.63 |
| H | O-F | 6.8 to 7.4 (m, 12H, ArH), | C 66.52 | C 66.68 |
| | | 6.43 (t, J = 74Hz, 1H, OCHF2), | H 4.72 | H 4.80 |
| | | 6.30 and 6.34 (2S, 1H, —CH—CN), | N 2.98 | N 3.04 |
| | | 3.27 (d, J = 10Hz, 1H, CH—CH(CH3)2) | F 12.14 | F 12.05 |
| H | m-F | 6.5 to 7.5 (m, 12H, ArH), | C 66.52 | C 66.80 |
| | | 6.33 and 6.39 (2S, 1H, —CH—CN), | H 4.72 | H 4.77 |
| | | 6.47 (t, J = 74Hz, 1H, OCHF2), | N 2.98 | N 2.89 |
| | | 3.28 (d, J = 10Hz, 1H, CH—CH(CH3)2) | F 12.14 | F 11.93 |
| F | p-Cl | 6.8 to 7.5 (m, 12H, ArH), | C 61.97 | C 62.05 |
| | | 6.37 and 6.41 (2S, 1H, —CH—CN), | H 4.20 | H 4.25 |
| | | 3.33 (d, J = 10Hz, CH—CH(CH3)2), | N 2.78 | N 2.52 |
| | | 0.6 to 1.2 (4d, bH, isopropyl CH3) | | |
| F | p-CH3 | 6.8 to 7.4 (m, 12H, ArH), | C 67.07 | C 65.28 |
| | | 6.37 and 6.41 (2S, 1H, —CH—CN) | H 5.00 | H 5.18 |
| | | 2.40 (S, 3H, CH3) | N 2.90 | N 2.26 |
| F | p-OCH3 | 6.9 to 7.5 (m, 12H, ArH), | C 64.92 | C 64.04 |
| | | 6.25 and 6.30 (2S, 1H, CH—CN), | H 4.84 | H 4.87 |
| | | 3.63 (S, 3H, OCH3) | N 2.80 | N 2.65 |

Preparation of m-(m-Fluorophenoxy)benzaldehyde

Sodium salt of 3-fluorophenol is prepared by mixing 3-fluorophenol (15.13 g, 0.135 mol) and sodium methoxide (7.20 g, 0.135 mol) in pyridine (115 ml). The reaction is heated to 110° C. during which 34 ml of pyridine-methanol is distilled off. The reaction is cooled to 80° C. and m-bromobenzaldehyde (25.0 g, 0.135 mol) and copper (I) chloride (4.05 g, 0.049 mol) are added. The reaction mixture is refluxed overnight. The following day,

EXAMPLE 63

Preparation of α-Ethynyl-m-phenoxybenzyl alcohol

Acetylene is dried through three traps, dry-ice-acetone, concentrated sulfuric acid and calcium chloride, and bubbled at about 5 psi pressure into dry THF (100 ml) for 10 minutes. Ethyl magnesium bromide (commercial, 0.14 mol) is added drop after drop over 2 hours at such a rate that the evolution of ethane is slowly and steady. After the addition, acetylene is bubbled through for 15 minutes. m-Phenoxybenzaldehyde (27.7 g, 0.14 mol) in THF (25 ml) is added to the reaction of 15° to 20° C. The reaction is allowed to raise to room temperature and stirred overnight. The complex is decomposed with saturated ammonium chloride solution. The product is extracted with ether, washed with water and dried ($Na_2SO_4$). Evaporation of the solvents, followed by vacuum distillation using Kugelrohn gives the alcohol (21.5 g).

EXAMPLE 64

Preparation of α-Ethynyl-m-phenoxybenzyl α-isopropyl-4-trifluoromethoxyphenylacetate Using the above alcohol in Example 63 and α-isopropyl-4-trifluoromethoxyphenylacetic acid and following the procedures of Examples 15 and 17, the product is obtained as yellow gum. The NMR spectrum showed the characteristic alkynyl proton as a multiplat at 2.52 δ and benzylic protons at 6.35 δ.

Analysis calculated for $C_{27}H_{23}F_3O_4$: C 69.22; H 4.95; Found: C 68.17; H 4.11.

By a similar procedure, using the alcohol in Example 63 and α-isopropyl-4-difluoromethoxyphenylacetic acid, the α-Ethynyl-m-phenoxybenzyl α-isopropyl-4-difluoromethoxyphenylacetate is prepared.

Analysis calculated for $C_{27}H_{24}F_2O_4$: C 71.99; H 5.37; Found: C 71.59; H 5.53.

EXAMPLE 65

Resolution of α-Isopropyl-4-difluoromethoxyphenylacetic Acid

A warm solution (60° C.) of (−)-2-phenylamine (4.96 g) in aqueous ethanol (60% ethanol, 20 ml) is added to a warm solution (60° C.) of the racemic acid (20 g) in aqueous ethanol (60% ethanol, 50 ml) with magnetic stirring. As the solution is allowed to cool slowly to room temperature, the salt precipitates out as white crystalline solid. The mixture is allowed to stand overnight and the solids are collected by filtration, washed with aqueous ethanol (10 ml) and dried (9.5 g): m.p. 184°–188°. The resolved acid obtained from the above salt is found to have a rotation $[\alpha]_D^{R.T}=+37.1°$ ($CHCl_3$, C=1.439 g/100 ml). Two more crystallizations of the above salt from aqueous ethanol (60% ethanol) gives white needles, m.p. 185°–187° C., from which the resolved acid is obtained with $[\alpha]_D^{R.T}=+40.4°$ ($CHCl_3$, C=1.353 g/100 ml).

EXAMPLE 66

Preparation of (±)-α-Cyano-m-phenoxybenzyl (±)-α-isopropyl-4-difluoromethoxyphenylacetate The resolved (±)-acid obtained in the above example is converted to the ester using the procedures of Examples 15 and 16. $N_D^{23}=1.5432$; NMR ($CDCl_3$) δ 6.8 to 7.5 (m, 13H, ArH), 6.43 (t, J=74 Hz, 1H, $OCHF_2$), 6.30 and 6.23 (2S, 1H, CH—CN), 3.27 (d, J=1oJz, 1H, C$\underline{H}$—CH($CH_3$)$_2$).

EXAMPLE 67

Resolution of α-Isopropyl-4-trifluoromethoxyphenylacetic acid

A mixture of the racemic acid (26.2 g) and (−)-α-phenethylamine (12.1 g) in aqueous ethanol (60% ethanol, 2 l) is heated to dissolution on a steam bath and allowed to cool slowly to room temperature. The salt is collected by filtration and dried (16.9 g): m.p. 189°–193°. The salt is crystallized twice from aqueous ethanol (60% ethanol, 1 l and 600 ml respectively): m.p. 194°–196° (8.0 g). The (+)-acid is obtained by neutralization of the salt with dilute hydrochloric acid and extraction with ester and evaporation of the solvent: $[\alpha]_D^{R.T}=+35.5°$ ($CHCl_3$, C=6.0 g/100 ml).

EXAMPLE 68

Preparation of (+)-α-Cyano-m-phenoxybenzyl (+)-α-isopropyl-4-trifluoromethoxyphenylacetate By using the (+)-α-isopropyl-4-trifluoromethoxyphenylacetic acid and procedures of Examples 15 and 16, the product is obtained as pale yellow oil: $[\alpha]_D^{R.T}=6.1°$ ($CHCl_3$, C=5 g/100 ml).

EXAMPLE 69

Insecticidal Activity

The insecticidal activity of the compounds of this invention is demonstrated in the following tests, wherein Tobacco budworm, *Heliothis virescens* (Fabricius); Western Potato Leafhopper, *Empoasca abrupta* (DeLong) and Bean Aphid, *Aphis fabae* (Scopoli), are employed as test insect species. Procedures employed are as follows: Tobacco Budworm, *Heliothis virescens* (Fabricius).

First Instar

A cotton plant with two true leaves expanded is dipped for 3 seconds with agitation in a test solution (35% water/65% acetone) containing 300, 100 or 10 ppm of test compound. Each leaf is placed in a cup with a wick and a piece of cheesecloth infested with 50–100 newly hatched larvae is added before covering the cup with a lid. After 3 days at 80° F., 50% r.h., the cups are examined and the kill of newly hatched larvea noted. Data obtained are reported as percent killed in Table I. Bean Aphid, *Aphis fabae* (Scopoli).

Five cm fiber pots, each containing a nasturtium plant 2 L inches high and infested with 100 to 150 aphids 2 days earlier are placed on a 4 rpm turntable and sprayed with a 35% water/65% acetone solution containing 100, 10, 1.0 and 0.1 ppm of test compound for two revolutions using a DeVilbiss Atomizer and 20 psi air pressure. The spray tip is held about 15 cm from the plants and the spray directed so as to give complete coverage of the aphids and the plants. The sprayed plants are laid on their sides on white enamel trays. Mortality estimates are made after one day at 70° F., 50% r.h.

Data are reported as percent mortality determined at the rate indicated (Table I).

Western Potato Leafhopper, *Empoasca abrupta* (DeLong).

A Sieva lima bean plant with the primary leaf expanded to 3 to 4 inches is dipped into a 35% water/65% acetone solution containing 100, 10 or 1 ppm of test compound. The dipped plant is placed in the hood to dry and then a 2.5 cm piece of the tip of one leaf is cut off and placed in a 4-inch petri dish with a moist filter paper in the bottom. From 3 to 10 second-instar nymphs are placed in the dish and the dish is then covered. Mortality counts are made after holding the thus-prepared dishes for 2 days at 80° F. and 50% r.h. Data obtained are reported in Table I. In these tests, permethrin is used as a standard or check.

TABLE I

Insecticidal Evaluation

| | % Mortality | | | | | | | | | |
|---|---|---|---|---|---|---|---|---|---|---|
| | Tobacco Budworm Larvae 1st Instar | | | Leafhopper | | | Aphids | | | |
| Compound | 300 ppm | 100 ppm | 10 ppm | 100 ppm | 10 ppm | 1 ppm | 100 ppm | 10 ppm | 1 ppm | 0.1 ppm |
| CF$_3$O—C$_6$H$_4$—CH(CH(CH$_3$)$_2$)—CO—O—CH(CN)—C$_6$H$_4$—O—C$_6$H$_5$ | 100 | 100 | 100 | 100 | 100 | 70 | 100 | 100 | 90 | 50 |
| CHF$_2$CF$_2$O—C$_6$H$_4$—CH(CH(CH$_3$)$_2$)—CO—O—CH$_2$—C$_6$H$_4$—O—C$_6$H$_5$ | 90 | 90 | 0 | 50 | 0 | — | 100 | 100 | 0 | — |
| CHF$_2$CF$_2$O—C$_6$H$_4$—CH(CH(CH$_3$)$_2$)—CO—O—CH(CN)—C$_6$H$_4$—O—C$_6$H$_5$ | 100 | 100 | 0 | 100 | 0 | — | 100 | 100 | 50 | — |
| F$_3$CS—C$_6$H$_4$—CH(CH(CH$_3$)$_2$)—CO—O—CH(CN)—C$_6$H$_4$—O—C$_6$H$_5$ | 100 | 100 | 61 to 70 | 100 | 100 | — | 100 | 100 | 80 | — |
| F$_2$CHS—C$_6$H$_4$—CH(CH(CH$_3$)$_2$)—CO—O—CH(CN)—C$_6$H$_4$—O—C$_6$H$_5$ | 100 | 71 to 85 | 0 to 40 | 70 | 0 | — | 100 | 100 | 50 | — |
| F$_2$CHO—C$_6$H$_4$—CH(CH(CH$_3$)$_2$)—CO—O—CH$_2$—C$_6$H$_4$—O—C$_6$H$_5$ | 100 | 100 | 0 to 40 | 100 | 0 | — | 100 | 100 | 0 | — |
| F$_2$CHO—C$_6$H$_4$—CH(CH(CH$_3$)$_2$)—CO—O—CH(CN)—C$_6$H$_4$—O—C$_6$H$_5$ | 100 | 100 | 86 to 99 | 100 | 100 | — | 100 | 100 | 100 | — |
| F$_3$CO—C$_6$H$_4$—CH(CH(CH$_3$)$_2$)—CO—O—CH$_2$—C$_6$H$_4$—O—C$_6$H$_5$ | 100 | 100 | 0 to 40 | 100 | 0 | — | 100 | 100 | 100 | — |
| F$_3$CO—C$_6$H$_4$—CH(CH$_2$CH$_3$)—CO—O—CH(CN)—C$_6$H$_4$—O—C$_6$H$_5$ | 100 | 100 | 61 to 70 | 100 | 70 | — | 100 | 100 | 100 | — |
| F$_3$CO—C$_6$H$_4$—CH(CH$_2$CH$_2$CH$_3$)—CO—O—CH$_2$—C$_6$H$_4$—O—C$_6$H$_5$ | 100 | 86 to 99 | 0 to 40 | 100 | 0 | — | — | 0 | — | — |
| F$_3$CO—C$_6$H$_4$—CH(CH$_2$CH$_2$CH$_3$)—CO—O—CH(CN)—C$_6$H$_4$—O—C$_6$H$_5$ | 100 | 100 | 71 to 85 | 100 | 50 | — | 100 | 90 | 90 | — |
| F$_2$CHO—C$_6$H$_4$—CH(CH(CH$_3$)$_2$)—CO—O—CH(CN)—C$_6$H$_4$—O—C$_6$H$_4$—Cl | 100 | 100 | 100 | 100 | 100 | 0 | 100 | 100 | 100 | 0 |
| F$_2$CHO—C$_6$H$_4$—CH(CH(CH$_3$)$_2$)—CO—O—CH(CN)—C$_6$H$_4$—O—C$_6$H$_4$—OCH$_3$ | 100 | 100 | 0 | 100 | 90 | 0 | 100 | 100 | 75 | — |
| F$_2$CHO—C$_6$H$_4$—CH(CH(CH$_3$)$_2$)—CO—O—CH(CN)—C$_6$H$_4$—O—C$_6$H$_4$—CH$_3$ | 100 | 100 | 0 | 90 | 50 | 0 | 100 | 100 | 70 | — |
| F$_2$CHO—C$_6$H$_4$—CH(CH(CH$_3$)$_2$)—CO—O—CH(CN)—C$_6$H$_4$—O—C$_6$H$_4$—F | 100 | 100 | 100 | 100 | 0 | — | 100 | 100 | 90 | 0 |
| F$_2$CHO—C$_6$H$_4$—CH(CH(CH$_3$)$_2$)—CO—O—CH(CN)—C$_6$H$_4$—O—C$_6$H$_4$—F | 100 | 100 | 50 | 100 | 100 | 50 | 100 | 100 | 50 | 0 |

TABLE I-continued

Insecticidal Evaluation

| Compound | Tobacco Budworm Larvae 1st Instar | | | Leafhopper | | | Aphids | | | |
|---|---|---|---|---|---|---|---|---|---|---|
| | 300 ppm | 100 ppm | 10 ppm | 100 ppm | 10 ppm | 1 ppm | 100 ppm | 10 ppm | 1 ppm | 0.1 ppm |
| F$_2$CHO—⬡—CH(CH(CH$_3$)$_2$)—CO—O—CH(CN)—⬡—O—⬡-F (ortho) | 100 | 100 | 0 | 50 | — | — | 100 | 100 | 0 | — |
| F$_3$CO—⬡—CH(CH(CH$_3$)$_2$)—CO—O—CH(CN)—⬡—O—⬡-Cl | 100 | 100 | 100 | 100 | 100 | 80 | 100 | 100 | 90 | 0 |
| F$_3$CO—⬡—CH(CH(CH$_3$)$_2$)—CO—O—CH(CN)—⬡—O—⬡-CH$_3$ | 100 | 100 | 0 | 100 | 100 | 50 | 100 | 100 | 100 | 0 |
| F$_3$CO—⬡—CH(CH(CH$_3$)$_2$)—CO—O—CH(CN)—⬡—O—⬡-OCH$_3$ | 90 | 80 | 0 | 100 | 100 | 0 | 100 | 100 | 100 | 0 |
| F$_3$CO—⬡—CH(CH(CH$_3$)$_2$)—CO—O—CH(CN)—⬡—O—⬡-F | 100 | 100 | 100 | 100 | 60 | — | 100 | 100 | 100 | 0 |
| F$_3$CO—⬡—CH(CH(CH$_3$)$_2$)—CO—O—CH(C≡CH)—⬡—O—⬡ | 100 | 100 | 80 | 100 | 75 | — | 100 | 100 | 75 | — |
| F$_2$CHO—⬡—CH(CH(CH$_3$)$_2$)—CO—O—CH(C≡CH)—⬡—O—⬡ | 100 | 100 | 50 | 100 | 75 | — | 100 | 100 | 50 | — |
| F$_2$CHO—⬡(3-CH$_3$)—CH(CH(CH$_3$)$_2$)—CO—O—CH(CN)—⬡—O—⬡ | 100 | 100 | 100 | 100 | 100 | 100 | 100 | 100 | 90 | 0 |
| F$_2$CHO—⬡(Br)—CH(CH(CH$_3$)$_2$)—CO—O—CH$_2$—⬡—O—⬡ | 100 | 80 | 0 | 100 | 50 | — | 100 | 100 | 100 | 0 |
| F$_2$CHO—⬡(Br)—CH(CH(CH$_3$)$_2$)—CO—O—CH(CN)—⬡—O—⬡ | 100 | 100 | 100 | 100 | 75 | — | 100 | 100 | 75 | — |
| F$_2$CHO—⬡(Cl)—CH(CH(CH$_3$)$_2$)—CO—O—CH$_2$—⬡—O—⬡ | 100 | — | 0 | 90 | 50 | — | 100 | 100 | 100 | 0 |
| F$_2$CHO—⬡(Cl)—CH(CH(CH$_3$)$_2$)—CO—O—CH(CN)—⬡—O—⬡ | 100 | 100 | 100 | 100 | 100 | 100 | 100 | 100 | 100 | 100 |
| F$_2$CHO—⬡(Cl,Cl)—CH(CH(CH$_3$)$_2$)—CO—O—CH$_2$—⬡—O—⬡ | 100 | 80 | 0 | 100 | 0 | — | 100 | 100 | 50 | — |
| F$_2$CHO—⬡(Cl,Cl)—CH(CH(CH$_3$)$_2$)—CO—O—CH(CN)—⬡—O—⬡ | 100 | 100 | 100 | 100 | 100 | 0 | 100 | 100 | 100 | 0 |

TABLE I-continued

| | Insecticidal Evaluation | | | | | | | | | |
|---|---|---|---|---|---|---|---|---|---|---|
| | % Mortality | | | | | | | | | |
| | Tobacco Budworm Larvae 1st Instar | | | Leafhopper | | | Aphids | | | |
| Compound | 300 ppm | 100 ppm | 10 ppm | 100 ppm | 10 ppm | 1 ppm | 100 ppm | 10 ppm | 1 ppm | 0.1 ppm |
| (+) acid $F_2CHO-\langle\rangle-CH(CH(CH_3)_2)-CO-O-CH(CN)-\langle\rangle-O-\langle\rangle$ (+) alcohol | 100 | 100 | 100 | 100 | 90 | 0 | 100 | 100 | 100 | 0 |

— = Not Tested.

EXAMPLE 70

Insecticidal Activity

The insecticidal activity of the compounds of the present invention is further demonstrated by the following tests.

The procedures employed for evaluation against mosquito larvae, Mexican Bean Beetles and Southern Armyworms are as follows:

Malaria Mosquito, *Anopheles quadrimaculatus* (Say)

One milliliter of a 35% water/65% acetone solution containing 300 ppm of test compound is pipetted in a 400 ml beaker containing 250 ml of deionized water and stirred with the pipette, giving a concentration of 1.2 ppm. Aliquots of this solution are taken and further diluted to 0.4, 0.04 and 0.004 ppm. A wax paper ring 0.6 cm wide to fit inside the beaker is floated on the surface of the test solution to keep the eggs from floating up the meniscus curve and drying out on the side of the glass. A spoon made of screen is used to scoop up and transfer about 100 eggs (0–24 hours old) into the test beaker. After 2 days at 80° F., 50% r.h., observations of hatching are made. Percent mortality records are presented in Table II.

Mexican Bean Beetle, *Epilachna varivestis* (Mulsant)

Sieva lima bean plants (2 per pot) with primary leaves 7.5 to 10 cm long, are dipped in the 300, 100, 10 or 1 ppm test solution and set in the hood to dry. One leaf is removed from a plant and placed in a 10 cm petri dish containing a moist filter paper on the bottom and 10 last-instar larvae (13 days from hatching). The day after treatment, another leaf is removed from the plant and fed to the larvae after removing the remains of the original leaf. Two days after treatment, the third leaf is fed to the larvae, this usually being the last needed. The fourth leaf is used on the third day after treatment if the larvae have not finished feeding. The test is now set aside and held until adults have emerged, usually in about 9 days after treatment began. After emergence is complete, each dish is examined for dead larvae, pupae or adults; deformed pupae or adults; larval-pupal intermediates or pupal-adult intermediates; or any other interference with normal molting, transformation and emergence of pupae or adults.

Data obtained are reported in Table II.

Southern Arymworm, *Spodoptera eridania* (Cramer)

Methods:

Sieva lima bean plants, with two expanded 7.5 to 10 cm primary leaves, are dipped three seconds with agitation in the treatment solutions and then set in a hood to dry. After the leaves are dry they are excised and each excised leaf is placed in a 10 cm petri dish containing a piece of moist filter paper and 10 third-instar southern arymworm larvae approximately 1 cm long. The petri dishes are covered and placed in a holding room for 2 days at a temperature of 80° F. and 50% relative humidity.

Mortality counts are made after 2 days. Results obtained are presented in Table II.

TABLE II

| | Insecticidal Evaluation | | | | | | | | | | |
|---|---|---|---|---|---|---|---|---|---|---|---|
| | % Mortality | | | | | | | | | | |
| | Mosquito Larvae | | | | Southern Armyworm | | | Mexican Bean Beetle | | | |
| Compound | 1.2 ppm | 0.4 ppm | 0.04 ppm | 0.004 ppm | 1000 ppm | 100 ppm | 10 ppm | 300 ppm | 100 ppm | 10 ppm | 1 ppm |
| $CF_3O-\langle\rangle-CH(CH(CH_3)_2)-CO-O-CH(CN)-\langle\rangle-O-\langle\rangle$ | 100 | 100 | 100 | 90 | 100 | 100 | 100 | 100 | 100 | 100 | 100 |
| $CHF_2CF_2O-\langle\rangle-CH(CH(CH_3)_2)-CO-O-CH_2-\langle\rangle-O-\langle\rangle$ | 100 | 100 | 90 | 0 | 100 | 100 | 0 | 100 | — | — | — |
| $CHF_2CF_2O-\langle\rangle-CH(CH(CH_3)_2)-CO-O-CH(CN)-\langle\rangle-O-\langle\rangle$ | 100 | 100 | 80 | 0 | 100 | 100 | 0 | 100 | — | — | — |

TABLE II-continued

Insecticidal Evaluation

| Compound | Mosquito Larvae | | | | Southern Armyworm | | | Mexican Bean Beetle | | | |
|---|---|---|---|---|---|---|---|---|---|---|---|
| | 1.2 ppm | 0.4 ppm | 0.04 ppm | 0.004 ppm | 1000 ppm | 100 ppm | 10 ppm | 300 ppm | 100 ppm | 10 ppm | 1 ppm |
| F$_3$CS—C$_6$H$_4$—CH[CH(CH$_3$)$_2$]—CO—O—CH(CN)—C$_6$H$_4$—O—C$_6$H$_5$ | 100 | 100 | 86 to 99 | — | 100 | 100 | 0 | 100 | 100 | 100 | — |
| F$_2$CHS—C$_6$H$_4$—CH[CH(CH$_3$)$_2$]—CO—O—CH(CN)—C$_6$H$_4$—O—C$_6$H$_5$ | 100 | 86 to 99 | 86 to 99 | — | 100 | 90 | 0 | 100 | 100 | 90 | — |
| F$_2$CHO—C$_6$H$_4$—CH[CH(CH$_3$)$_2$]—CO—O—CH$_2$—C$_6$H$_4$—O—C$_6$H$_5$ | 100 | 100 | 100 | — | 100 | 100 | 0 | 100 | 90 | 50 | — |
| F$_2$CHO—C$_6$H$_4$—CH[CH(CH$_3$)$_2$]—CO—O—CH(CN)—C$_6$H$_4$—O—C$_6$H$_5$ | 100 | 100 | 100 | — | 100 | 100 | 100 | 100 | 100 | 50 | — |
| F$_3$CO—C$_6$H$_4$—CH(CH$_2$CH$_3$)—CO—O—CH$_2$—C$_6$H$_4$—O—C$_6$H$_5$ | 100 | 100 | 100 | — | 100 | 100 | 70 | 90 | 0 | 0 | — |
| F$_3$CO—C$_6$H$_4$—CH(CH$_2$CH$_3$)—CO—O—CH(CN)—C$_6$H$_4$—O—C$_6$H$_5$ | 100 | 100 | 100 | — | 100 | 100 | 100 | 80 | 90 | 50 | — |
| F$_3$CO—C$_6$H$_4$—CH(CH$_2$CH$_2$CH$_3$)—CO—O—CH$_2$—C$_6$H$_4$—O—C$_6$H$_5$ | 100 | 100 | 100 | — | 100 | 100 | 0 | 100 | 90 | 0 | — |
| F$_3$CO—C$_6$H$_4$—CH(CH$_2$CH$_2$CH$_3$)—CO—O—CH(CN)—C$_6$H$_4$—O—C$_6$H$_5$ | 100 | 100 | 100 | — | 100 | 100 | 70 | 100 | 100 | 100 | — |
| (3-CF$_3$O)C$_6$H$_4$—CH[CH(CH$_3$)$_2$]—CO—O—CH(CN)—C$_6$H$_4$—O—C$_6$H$_5$ | 100 | 100 | 100 | 0 | 100 | 100 | 0 | 100 | 100 | 100 | 80 |
| F$_2$CHO—C$_6$H$_4$—CH[CH(CH$_3$)$_2$]—CO—O—CH(CN)—C$_6$H$_4$—O—C$_6$H$_4$—Cl | 100 | 100 | 100 | 80 | 100 | 90 | 0 | 100 | 40 | 0 | 0 |
| F$_2$CHO—C$_6$H$_4$—CH[CH(CH$_3$)$_2$]—CO—O—CH(CN)—C$_6$H$_4$—O—C$_6$H$_4$—OCH$_3$ | 80 | 100 | 100 | 80 | 100 | 100 | 0 | 90 | 90 | 0 | — |
| F$_2$CHO—C$_6$H$_4$—CH[CH(CH$_3$)$_2$]—CO—O—CH(CN)—C$_6$H$_4$—O—C$_6$H$_4$—CH$_3$ | 100 | 100 | 100 | 80 | 100 | 0 | 0 | 100 | 80 | 0 | — |
| F$_2$CHO—C$_6$H$_4$—CH[CH(CH$_3$)$_2$]—CO—O—CH(CN)—C$_6$H$_4$—O—C$_6$H$_4$—F | 100 | 100 | 100 | 100 | 100 | 100 | 90 | 100 | 50 | 0 | — |
| F$_2$CHO—C$_6$H$_4$—CH[CH(CH$_3$)$_2$]—CO—O—CH(CN)—C$_6$H$_4$—O—C$_6$H$_4$—F (3-F) | 100 | 100 | 100 | 50 | 100 | 100 | 40 | 100 | 100 | 100 | 0 |
| F$_2$CHO—C$_6$H$_4$—CH[CH(CH$_3$)$_2$]—CO—O—CH(CN)—C$_6$H$_4$—O—C$_6$H$_4$—F (2-F) | 100 | 100 | 100 | 0 | 100 | 100 | 0 | 100 | 100 | 100 | 0 |

TABLE II-continued

Insecticidal Evaluation

| Compound | Mosquito Larvae % Mortality | | | | Southern Armyworm % Mortality | | | Mexican Bean Beetle % Mortality | | | |
|---|---|---|---|---|---|---|---|---|---|---|---|
| | 1.2 ppm | 0.4 ppm | 0.04 ppm | 0.004 ppm | 1000 ppm | 100 ppm | 10 ppm | 300 ppm | 100 ppm | 10 ppm | 1 ppm |
| $F_3CO$-C$_6$H$_4$-CH(CH(CH$_3$)$_2$)-CO-O-CH(CN)-C$_6$H$_3$(-O-C$_6$H$_4$-Cl) | 100 | 100 | 100 | 100 | 100 | 100 | 60 | 100 | 100 | 100 | 0 |
| $F_3CO$-C$_6$H$_4$-CH(CH(CH$_3$)$_2$)-CO-O-CH(CN)-C$_6$H$_4$-O-C$_6$H$_4$-CH$_3$ | 100 | 100 | 80 | — | 100 | 50 | 0 | 100 | 100 | 50 | 0 |
| $F_3CO$-C$_6$H$_4$-CH(CH(CH$_3$)$_2$)-CO-O-CH(CN)-C$_6$H$_4$-O-C$_6$H$_4$-OCH$_3$ | 100 | 100 | 100 | 0 | 100 | 100 | 0 | 100 | 100 | 50 | 0 |
| $F_3CO$-C$_6$H$_4$-CH(CH(CH$_3$)$_2$)-CO-O-CH(CN)-C$_6$H$_4$-O-C$_6$H$_4$-F | 100 | 100 | 100 | 100 | 100 | 100 | 100 | 100 | 80 | 40 | 0 |
| $F_3CO$-C$_6$H$_4$-CH(CH(CH$_3$)$_2$)-CO-O-CH(C≡CH)-C$_6$H$_4$-O-C$_6$H$_5$ | 100 | — | — | — | 100 | 100 | 0 | 100 | — | — | — |
| $F_2CHO$-C$_6$H$_4$-CH(CH(CH$_3$)$_2$)-CO-O-CH(C≡CH)-C$_6$H$_4$-O-C$_6$H$_5$ | 100 | — | — | — | 100 | 90 | 0 | 100 | — | — | — |
| $F_2CHO$-C$_6$H$_3$(3-CH$_3$)-CH(CH(CH$_3$)$_2$)-CO-O-CH(CN)-C$_6$H$_4$-O-C$_6$H$_5$ | 100 | 100 | 100 | 100 | 100 | 100 | 20 | 100 | 100 | 90 | 0 |
| $F_2CHO$-C$_6$H$_3$(Br)-CH(CH(CH$_3$)$_2$)-CO-O-CH$_2$-C$_6$H$_4$-O-C$_6$H$_5$ | 100 | — | — | — | 100 | 100 | 0 | 100 | — | — | — |
| $F_2CHO$-C$_6$H$_3$(Br)-CH(CH(CH$_3$)$_2$)-CO-O-CH(CN)-C$_6$H$_4$-O-C$_6$H$_5$ | 100 | — | — | — | 100 | 100 | 0 | 100 | — | — | — |
| $F_2CHO$-C$_6$H$_3$(Cl)-CH(CH(CH$_3$)$_2$)-CO-O-CH$_2$-C$_6$H$_4$-O-C$_6$H$_5$ | 100 | 100 | 80 | 50 | 100 | 0 | 0 | 0 | — | — | — |
| $F_2CHO$-C$_6$H$_3$(Cl)-CH(CH(CH$_3$)$_2$)-CO-O-CH(CN)-C$_6$H$_4$-O-C$_6$H$_5$ | 80 | 100 | 100 | 0 | 100 | 100 | 70 | 100 | — | — | — |
| $F_2CHO$-C$_6$H$_2$(Cl)$_2$-CH(CH(CH$_3$)$_2$)-CO-O-CH$_2$-C$_6$H$_4$-O-C$_6$H$_5$ | 100 | — | — | — | 100 | 90 | 0 | 100 | — | — | — |
| $F_2CHO$-C$_6$H$_2$(Cl)$_2$-CH(CH(CH$_3$)$_2$)-CO-O-CH(CN)-C$_6$H$_4$-O-C$_6$H$_5$ | 100 | — | — | — | 100 | 100 | 0 | 100 | — | — | — |

TABLE II-continued

| | Insecticidal Evaluation | | | | | | | | | | |
|---|---|---|---|---|---|---|---|---|---|---|---|
| | % Mortality | | | | | | | | | | |
| | Mosquito Larvae | | | | Southern Armyworm | | | Mexican Bean Beetle | | | |
| Compound | 1.2 ppm | 0.4 ppm | 0.04 ppm | 0.004 ppm | 1000 ppm | 100 ppm | 10 ppm | 300 ppm | 100 ppm | 10 ppm | 1 ppm |
| (+)acid F₂CHO—⟨⟩—CH(CH(CH₃)₂)—CO—O—CH(CN)(±)alcohol—⟨⟩—O—⟨⟩ | 100 | 100 | 100 | 100 | 100 | 100 | 100 | 100 | 100 | 100 | 50 |

— = Not Tested.

EXAMPLE 71

Insecticidal Activity

Two-Spotted Spider Mite, *Tetranychus urticae* (Koch)

Sieva lima bean plants, with primary leaves three 7.5 to 10 cm long, are infected with about 100 adult phosphate-resistant mites per leaf 4 hours before use in this test, in order to allow egg laying before treatment. The infested plants are dipped for 3 seconds with agitation into the 1000, 300, 100 or 10 ppm solution, and the plants set in the hood to dry. After 2 days at 80° F., the adult mite mortality is estimated on one leaf under a 10× stereoscopic microscope. The other leaf is left on the plant an additional 5 days and then examined at 10× power to estimate the kill of eggs and of newly hatched nymphs, giving a measure of ovicidal and residual action, respectively. Test results are provided in Table III.

Tobacco Budworm, *Heliothis virescens* (Fabricus)

Third Instar

Three cotton plants with just expanded cotyledons are dipped in 1000 or 100 ppm solution and placed in the hood to dry. When dry, each cotyledon is cut in half, and 10 leaf sections are each placed in a 28 g plastic medicine cup containing a 1.25 cm dental wick saturated with water and one third-instar budworm larva is added. The cup is capped and held for 3 days at 80° F., 50% r.h., after which mortality counts are made. Test results are provided in Table III.

Cabbage Looper, *Trichoplusia ni* (Hübner)

Third Instar

A true leaf on a cotton plant is dipped into the test solution containing 1000, 100 or 10 ppm of test compound, agitated for 3 seconds, and removed to dry in an exhaust hood. When dry, the leaf is placed in a 9.0 cm petri dish with moist filter paper on the bottom. Ten third-instar larvae are added and the lid placed on the dish. Mortality counts are made after 3 days at 80° F. and 50±10% r.h.

Data obtained are reported in Table III below.

TABLE III

| | Insecticidal Activity | | | | | | | | |
|---|---|---|---|---|---|---|---|---|---|
| | % Mortality | | | | | | | | |
| | Phosphate-Resistant Mites | | | | 3rd Instar Tobacco Budworm | | 3rd Instar Cabbage Looper | | |
| Compound | 1000 ppm | 300 ppm | 100 ppm | 10 ppm | 1000 ppm | 100 ppm | 1000 ppm | 100 ppm | 10 ppm |
| CF₃O—⟨⟩—CH(CH(CH₃)₂)—CO—O—CH(CN)—⟨⟩—O—⟨⟩ | 100 | 100 | 80 | 0 | 100 | 100 | 100 | 100 | 100 |
| CHF₂CF₂O—⟨⟩—CH(CH(CH₃)₂)—CO—O—CH₂—⟨⟩—O—⟨⟩ | — | 100 | 50 | 0 | 50 | 1 | 100 | 0 | — |
| CHF₂CF₂O—⟨⟩—CH(CH(CH₃)₂)—CO—O—CH(CN)—⟨⟩—O—⟨⟩ | — | 90 | 60 | 0 | 80 | 0 | 100 | 30 | 0 |
| F₃CS—⟨⟩—CH(CH(CH₃))—CO—O—CH(CN)—⟨⟩—O—⟨⟩ | — | 100 | 100 | 100 | 100 | 100 | 100 | 100 | — |
| F₂CHS—⟨⟩—CH(CH(CH₃)₂)—CO—O—CH(CN)—⟨⟩—O—⟨⟩ | — | 100 | 100 | 0 | 90 | 20 | 100 | 100 | — |
| F₂CHO—⟨⟩—CH(CH(CH₃)₂)—CO—O—CH₂—⟨⟩—O—⟨⟩ | — | 100 | 0 | 0 | 100 | 70 | 100 | 100 | — |
| F₂CHO—⟨⟩—CH(CH(CH₃)₂)—CO—O—CH(CN)—⟨⟩—O—⟨⟩ | — | 100 | 100 | 0 | 100 | 100 | 100 | 100 | — |

TABLE III-continued

Insecticidal Activity

| Compound | Phosphate-Resistant Mites | | | | 3rd Instar Tobacco Budworm | | 3rd Instar Cabbage Looper | | |
|---|---|---|---|---|---|---|---|---|---|
| | 1000 ppm | 300 ppm | 100 ppm | 10 ppm | 1000 ppm | 100 ppm | 1000 ppm | 100 ppm | 10 ppm |
| $F_3CO$-C$_6H_4$-CH(CH$_2$CH$_3$)-CO-O-CH$_2$-C$_6H_4$-O-C$_6H_5$ | — | 100 | 0 | — | 100 | 100 | 100 | 100 | — |
| $F_3CO$-C$_6H_4$-CH(CH$_2$CH$_3$)-CO-O-CH(CN)-C$_6H_4$-O-C$_6H_5$ | — | 100 | 100 | 0 | 100 | 100 | 100 | 100 | — |
| $F_3CO$-C$_6H_4$-CH(CH$_2$CH$_2$CH$_3$)-CO-O-CH$_2$-C$_6H_4$-O-C$_6H_5$ | — | 80 | 0 | — | 60 | 30 | 100 | 40 | — |
| $F_3CO$-C$_6H_4$-CH(CH$_2$CH$_2$CH$_3$)-CO-O-CH(CN)-C$_6H_4$-O-C$_6H_5$ | — | 100 | 100 | — | 90 | 90 | 100 | 100 | — |
| $CF_3O$-C$_6H_4$(meta)-CH(CH(CH$_3$)$_2$)-CO-O-CH(CN)-C$_6H_4$-O-C$_6H_5$ | — | 100 | 100 | 0 | 100 | 90 | 100 | 90 | 0 |
| $F_2CHO$-C$_6H_4$-CH(CH(CH$_3$)$_2$)-CO-O-CH(CN)-C$_6H_4$-O-C$_6H_4$-Cl | 100 | 0 | — | — | 100 | 40 | 100 | 100 | 60 |
| $F_2CHO$-C$_6H_4$-CH(CH(CH$_3$)$_2$)-CO-O-CH(CN)-C$_6H_4$-O-C$_6H_4$-OCH$_3$ | 100 | 0 | — | — | 50 | — | 100 | 100 | 0 |
| $F_2CHO$-C$_6H_4$-CH(CH(CH$_3$)$_2$)-CO-O-CH(CN)-C$_6H_4$-O-C$_6H_4$-CH$_3$ | 100 | 0 | — | — | 100 | 20 | 100 | 100 | 30 |
| $F_2CHO$-C$_6H_4$-CH(CH(CH$_3$)$_2$)-CO-O-CH(CN)-C$_6H_4$-O-C$_6H_4$-F (para) | 100 | 100 | 0 | — | 100 | 100 | 100 | 100 | 100 |
| $F_2CHO$-C$_6H_4$-CH(CH(CH$_3$)$_2$)-CO-O-CH(CN)-C$_6H_4$-O-C$_6H_4$-F (meta) | 100 | 60 | 0 | — | 100 | 100 | 100 | 100 | 100 |
| $F_2CHO$-C$_6H_4$-CH(CH(CH$_3$)$_2$)-CO-O-CH(CN)-C$_6H_4$-O-C$_6H_4$-F (ortho) | 0 | — | — | — | 100 | 60 | 100 | 100 | 0 |
| $F_3CO$-C$_6H_4$-CH(CH(CH$_3$)$_2$)-CO-O-CH(CN)-C$_6H_4$-O-C$_6H_4$-Cl | 100 | 100 | 60 | 0 | 100 | 80 | 100 | 100 | 100 |
| $F_3CO$-C$_6H_4$-CH(CH(CH$_3$)$_2$)-CO-O-CH(CN)-C$_6H_4$-O-C$_6H_4$-CH$_3$ | 100 | 100 | 0 | — | 100 | 30 | 100 | 100 | 0 |
| $F_2CHO$-C$_6H_4$-CH(CH(CH$_3$)$_2$)-CO-O-CH(CN)-C$_6H_4$-O-C$_6H_4$-F | 100 | 60 | 0 | — | 100 | 100 | 100 | 100 | 100 |
| $F_2CHO$-C$_6H_4$-CH(CH(CH$_3$)$_2$)-CO-O-CH(CN)-C$_6H_4$-O-C$_6H_4$-F (ortho) | 0 | — | — | — | 100 | 60 | 100 | 100 | 0 |
| $F_3CO$-C$_6H_4$-CH(CH(CH$_3$)$_2$)-CO-O-CH(CN)-C$_6H_4$-O-C$_6H_4$-Cl | 100 | 100 | 60 | 0 | 100 | 80 | 100 | 100 | 100 |

TABLE III-continued

Insecticidal Activity

| Compound | Phosphate-Resistant Mites % Mortality | | | | 3rd Instar Tobacco Budworm % Mortality | | 3rd Instar Cabbage Looper % Mortality | | |
|---|---|---|---|---|---|---|---|---|---|
| | 1000 ppm | 300 ppm | 100 ppm | 10 ppm | 1000 ppm | 100 ppm | 1000 ppm | 100 ppm | 10 ppm |
| F₃CO—⟨⟩—CH(CH(CH₃)₂)—CO—O—CH(CN)—⟨⟩—O—⟨⟩—CH₃ | 100 | 100 | 0 | — | 100 | 30 | 100 | 100 | 0 |
| F₃CO—⟨⟩—CH(CH(CH₃)₂)—CO—O—CH(CN)—⟨⟩—O—⟨⟩—OCH₃ | 100 | 100 | 0 | — | 100 | 80 | 100 | 100 | 90 |
| F₃CO—⟨⟩—CH(CH(CH₃)₂)—CO—O—CH(CN)—⟨⟩—O—⟨⟩—F | 100 | 100 | 80 | — | 100 | 100 | 100 | 100 | 100 |
| F₃CO—⟨⟩—CH(CH(CH₃)₂)—CO—O—CH(C≡CH)—⟨⟩—O—⟨⟩ | 100 | 100 | 0 | — | 100 | 50 | 100 | 70 | 0 |
| F₂CHO—⟨⟩—CH(CH(CH₃)₂)—CO—O—CH(C≡CH)—⟨⟩—O—⟨⟩ | 100 | 100 | 0 | — | 100 | 50 | 100 | 50 | 0 |
| F₂CHO—⟨CH₃⟩—CH(CH(CH₃)₂)—CO—O—CH(CN)—⟨⟩—O—⟨⟩ | 100 | 0 | 0 | — | 100 | 80 | 100 | 100 | 50 |
| F₂CHO—⟨Br⟩—CH(CH(CH₃)₂)—CO—O—CH₂—⟨⟩—O—⟨⟩ | 100 | 0 | — | — | 90 | 30 | 90 | 50 | — |
| F₂CHO—⟨⟩—CH(CH(CH₃)₂)—CO—O—CH(CN)—⟨⟩—O—⟨⟩ | 100 | 100 | 0 | — | 100 | 80 | 100 | 60 | — |
| F₂CHO—⟨Cl⟩—CH(CH(CH₃)₂)—CO—O—CH—⟨⟩—O—⟨⟩ | 100 | — | 0 | — | 100 | 100 | 100 | 0 | 0 |
| F₂CHO—⟨Cl⟩—CH(CH(CH₃)₂)—CO—O—CH(CN)—⟨⟩—O—⟨⟩ | 100 | 100 | 0 | — | 100 | 90 | 100 | 100 | 100 |
| F₂CHO—⟨Cl,Cl⟩—CH(CH(CH₃)₂)—CO—O—CH₂—⟨⟩—O—⟨⟩ | 100 | 50 | — | — | 90 | 10 | 100 | 80 | 0 |
| F₂CHO—⟨Cl,Cl⟩—CH(CH(CH₃)₂)—CO—O—CH(CN)—⟨⟩—O—⟨⟩ | 100 | 90 | 0 | — | 100 | 40 | 100 | 100 | 70 |
| (+)acid F₂CHO—⟨⟩—CH(CH(CH₃)₂)—CO—O—CH(CN(±)alcohol)—⟨⟩—O—⟨⟩ | 100 | 100 | 0 | — | 100 | 100 | 100 | 100 | 100 |

— = Not Tested.

EXAMPLE 72

Soil Insecticidal Activity

Southern Corn Rootworm, *Diabrotica undecimpunctata howardi* (Barber)

Ten (10) mg of compound are diluted to 10 ml with acetone to make a stock solution (A). Two (2) ml of this solution is then diluted to 10 ml with acetone to make solution B. Approximately 0.7 g Pyrax ABB talc is then placed in a 28 g widemouth jar and 1.25 ml of the selected solution is added to the talc to produce the following concentrations:

1.25 ml solution A yields 56 kg/ha
1.25 ml solution B yields 11.2 kg/ha

The selected test solution is mixed with the talc to wet it evenly before it is dried under an air-jet dryer for 10-15 minutes. Twenty-five (25) ml of moist sterilized potting soil and approximately 0.6 g millet speed (food for larvae) are then added to the jars containing test compound. The jars are capped and the contents mixed on a vibrating mixer. Each jar then receives 10 southern corn rootworm larvae which are 6-8 days old. The jars are loosely capped and placed in a holding room at 80° F. and 50% r.h. with constant light. Mortality counts are made after 6 days.

In this test, α-cyano-m-phenoxybenzyl, α-isopropyl-4-trifluoromethoxyphenylacetate gave 100% control of southern corn rootworms at the 56 kg/ha rate and 70% control at the 11.2 kg/ha rate.

EXAMPLE 73

Residual Insecticidal Activity Obtained with Foliar Treatment of Cotton Plants Young cotton plants with at least two expanded true leaves growing in 10 cm plastic pots were dipped, usually one leaf at a time, in a 65% acetone/35% water solution of test compound with agitation for 3 seconds. The concentration of each compound in the solutions was 30 ppm, 100 ppm, 300 ppm or 900 ppm of active ingredient.

After the leaves had dried, two leaves from each of two plants were excised and placed in petri dishes (90 mm × 10 mm) on moist filter paper (9 cm Whatman No. 1). Five third-instar tobacco budworm larvae were placed on each leaf and the petri dish capped. The infested dishes were then placed in the holding room with continuous light, ambient temperature of 80° F. and 50% r.h. Larval counts were made after 72 hours.

The remaining plants were placed under high intensity lights in the greenhouse adjusted to provide 14 hours of light per day. Leaf samples were assayed with third-instar tobacco budworm larve after 3, 7, 10 and 14 days exposure in the greenhouse.

TABLE IV

Residual Insecticidal Activity of Test Compounds on Cotton Plants Using Third-Instar Tobacco Budworm Larvae for Bioassay

| Compound | Rate ppm | Days Residual Activity | | | | | | | | | |
|---|---|---|---|---|---|---|---|---|---|---|---|
| | | 0 | | 3 | | 7 | | 10 | | 14 | |
| | | 1* | 2** | 1* | 2** | 1* | 2** | 1* | 2** | 1* | 2** |
| 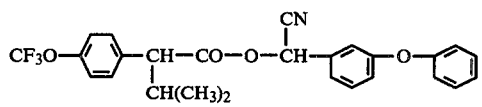 | 30 | 90 | 0 | 90 | 0 | 60 | 0 | 60 | 0.03 | 60 | 1.3 |
| | 100 | 100 | 0 | 100 | 0 | 100 | 0 | 95 | 0 | 95 | 0.03 |
| | 300 | 100 | 0 | 100 | 0 | 100 | 0 | 100 | 0 | 100 | 0 |
| | 900 | 100 | 0 | 100 | 0 | 100 | 0 | 100 | 0 | 100 | 0 |
| 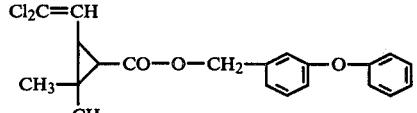 Permethrin | 30 | 65 | 0.3 | 30 | 11.3 | 15 | 12.5 | 40 | 4.3 | 5 | 57.5 |
| | 100 | 85 | 0 | 85 | 0.03 | 70 | 0.53 | 65 | 0.6 | 25 | 1.0 |
| | 300 | 100 | 0 | 100 | 0 | 100 | 0 | 95 | 0 | 80 | 0 |
| | 900 | 100 | 0 | 100 | 0 | 100 | 0 | 90 | 0 | 100 | 0 |
| 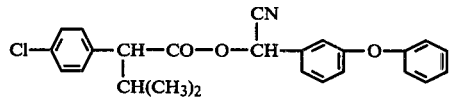 South Africa 73/4462 | 30 | 65 | 0.03 | 65 | 0.1 | 75 | 0.05 | 45 | 2.3 | 75 | 0.03 |
| | 100 | 100 | 0 | 85 | 0 | 100 | 0 | 90 | 0.03 | 100 | 0 |
| | 300 | 95 | 0 | 100 | 0 | 100 | 0 | 95 | 0 | 95 | 0 |
| | 900 | 100 | 0 | 100 | 0 | 100 | 0 | 100 | 0 | 100 | 0 |
| Check | — | 0 | 100 | 0 | 96.3 | 5 | 90 | 0 | 73.8 | 13 | 80 |

1* = Average % Mortality 20 TBW/Point.
2** = Average % Feeding Damage.

EXAMPLE 74

Ixodicidal Activity

Effective control of acarina larvae is demonstrated in the following tests with larvae of *Boophilus microplus*, a one-host tick which can remain on a single host through its three life stages; i.e., larvae, nymph and adult. In these tests, a 10% acetone/90% water mixture contains 0.025, 0.1, 0.5, 2.5 or 12.5 ppm of test compound. Twenty (20) larvae are enclosed in a pipette sealed at one end with a gauze material and solution containing the test compound is then drawn through the pipette with a vacuum hose, thereby simulating a spray system. The ticks are then held for 48 hours at room temperature and mortality is determined. The results achieved are set forth below.

TABLE V

Percent Larval Tick Mortality of *Boophilus microplus* Larvae

| Compound | ppm | | | | |
|---|---|---|---|---|---|
| | 12.5 | 2.5 | 0.5 | 0.1 | 0.025 |
|  | 100 | 100 | 100 | 100 | 100 |

The above procedure is repeated excepting that the concentration of test compound is 0.1, 0.025, 0.005 or 0.001.

TABLE VI

Percent Mortality of *Boophilus microplus* Larvae

| Compound | ppm | | | |
|---|---|---|---|---|
| | 0.1 | 0.025 | 0.005 | 0.001 |
| 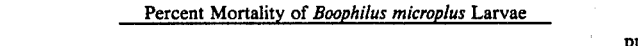 | 100 | 100 | 80 | 80 |

The above procedure is repeated, excepting that the concentration of test compound is 0.1, 0.01, 0.001, 0.0001 or 0.00001.

TABLE VIa

Percent Mortality of *Boophilus microplus* Larvae

Compound $F_2CHO-\langle\text{Ar}\rangle-CH(CH(CH_3)_2)-CO-O-CH(CN)-\langle\text{Ar}\rangle-O-\langle\text{Ar}\rangle$

| 0.1 ppm | 0.01 ppm | 0.001 ppm | 0.0001 ppm | 0.00001 ppm |
|---|---|---|---|---|
| 100 | 100 | 100 | 50 | 0 |

The above procedure is repeated, excepting that the concentration of test compound is 100.

TABLE VIb

Percent Mortality of *Boophilus microplus* Larvae

| Compound | 100 ppm |
|---|---|
| F₂CHS—⟨⟩—CH(CH(CH₃)₂)—CO—O—CH(CN)—⟨⟩—O—⟨⟩ | 100 |
| F₂CHO—⟨⟩—CH(CH(CH₃)₂)—CO—O—CH₂—⟨⟩—O—⟨⟩ | 100 |
| F₃CO—⟨⟩—CH(CH₂CH₃)—CO—O—CH₂—⟨⟩—O—⟨⟩ | 100 |
| F₃CO—⟨⟩—CH(CH₂CH₃)—CO—O—CH(CN)—⟨⟩—O—⟨⟩ | 100 |
| F₃CO—⟨⟩—CH(CH₂CH₂CH₃)—CO—O—CH(CN)—⟨⟩—O—⟨⟩ | 100 |

TABLE VIb-continued

Percent Mortality of *Boophilus microplus* Larvae

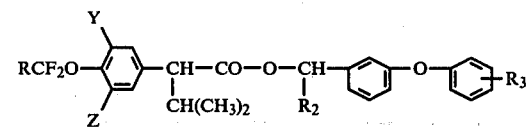

| R | Y | Z | R₂ | R₃ | % Mortality at-ppm |
|---|---|---|---|---|---|
| H | H | H | CN | p-Cl | 100 @ 100 ppm |
| H | H | H | CN | p-OCH₃ | 75 @ 100 |
| H | H | H | CN | p-CH₃ | 100 @ 100 |
| H | H | H | CN | p-F | 100 @ .1; 30 @ .01 |
| H | H | H | CN | m-F | 100 @ 100 |
| H | H | H | CN | o-F | 100 @ 100 |
| F | H | H | CN | p-Cl | 80 @ 100 |
| F | H | H | CN | p-CH₃ | 100 @ 0.1; 10 @ 0.01 |
| F | H | H | CN | p-OCH₃ | 90 @ 100 |
| F | H | H | CN | p-F | 75 @ .01; 20 @ .001 |
| F | H | H | —C≡CH | H | 100 @ 100 |
| H | H | H | —C≡CH | H | 100 @ 100 |
| H | CH₃ | H | CN | H | 0 @ 100 |
| H | Br | H | H | H | 0 @ 100 |
| H | Br | H | CN | H | 100 @ 700 |
| H | Cl | H | H | H | 100 @ 100 |
| H | Cl | H | CN | H | 75 @ 100 |
| H | Cl | Cl | H | H | 40 @ 100 |
| H | Cl | Cl | H | CN | 90 @ 100 |
| H | H | H | H | H | 100 @ 100 |
| F | H | H | H | H | 100 @ .004 |
| F | H | H | H | H | 100 @ 100 |
| α-ethyl F | H | H | H | H | 100 @ 100 |
| α-ethyl F | H | H | CN | H | 100 @ 100 |
| F | H | H | CN | H | 85 @ .00001 |
| H | H | H | CN | H | 95 @ 1 |
| | | | | | 70 @ .01 |
| | | | | | 25 @ .001 |

EXAMPLE 75

The effectiveness of the compounds of the invention for controlling adult *Boophilus microplus* ticks is determined in the following tests, wherein test compound is made up in solutions as described in Example 74, excepting that sufficient compound is used to give solutions containing 125, 52.6, 31.2, 15.6 or 7.3 ppm of test compound.

Adult engorged female ticks are then dipped in the test solutions for 3 seconds and placed in individual containers and held for 48 hours in a room maintained at 80° F. and 50% r.h. At the end of the holding period, the ticks are examined and egg deposits counted. Eggs are then left to hatch and final results are read in percent reduction of viable eggs. Engorged females that do not deposit eggs are considered dead. Data obtained are reported below in Table VII.

formulations (0.9 ml) containing 1, 5 or 25 ppm of test compound.

Two replicates of 20 larvae per dosage level are used in the evaluations. Larvae are permitted to feed *ad libitum* for 24 hours on the composition medium. After this period the number of dead larvae for each treatment and each replicate are determined and percent mortality calculated. Data obtained are reported in Table VIII below.

TABLE VII

Ixodicidal Activity Against Adult *Boophilus microplus*

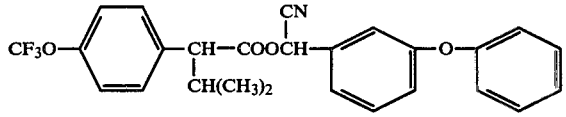

| Compound | Percent Adult Tick Mortality at Concentrations | | | | |
|---|---|---|---|---|---|
|  | 125 ppm | 62.5 ppm | 31.2 ppm | 15.6 ppm | 7.3 ppm |
| CF$_3$O—⌬—CH(CH(CH$_3$)$_2$)—COOCH(CN)—⌬—O—⌬ | 100 | 100 | 99.4 | 98.8 | 87.2 |

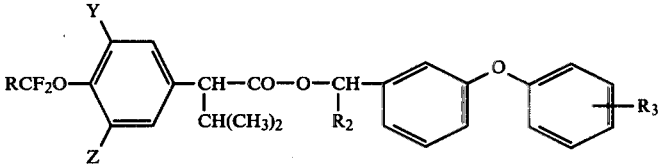

| R | Y | Z | R$_2$ | R$_3$ | Percent reduction of viable eggs at — ppm. |
|---|---|---|---|---|---|
| H | H | H | CN | p-Cl | 94 @ 125; 80 @ 31 ppm |
| H | H | H | CN | p-CH$_3$ | 85 @ 125; 52 @ 31 |
| H | H | H | CN | p-F | 94.9 @ 125; 37.9 @ 32 |
| H | H | H | CN | m-F | 94 @ 125; 52 @ 31 |
| H | H | H | CN | o-F | 99 @ 500; 65 @ 125 |
| F | H | H | CN | p-CH$_3$ | 89 @ 16; 73 @ 8 |
| F | H | H | CN | p-F | 96 @ 8; 49.6 @ 2 |
| H | H | H | H | H | 98 @ 15 |
| F | H | H | H | H | 67 @ .25 |
| F α-ethyl | H | H | H | H | 0 @ 500 |
| F α-ethyl | H | H | H | H | 0 @ 500 |
| F | H | H | CN | H | 0 @ 500 |
| F | H | H | CN | H | 98 @ 62; 47 @ 8 |

TABLE VIII

Evaluation of Compounds for the Control of Screw-worm Larvae, *Cochliomyia hominivorax*

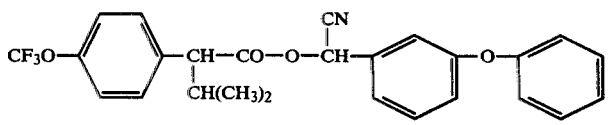

| Compound | Percent Mortality at Concentration | | |
|---|---|---|---|
|  | 1 ppm | 5 ppm | 25 ppm |
| CF$_3$O—⌬—CH(CH(CH$_3$)$_2$)—CO—O—CH(CN)—⌬—O—⌬ | 2.4 | 69.2 | 100 |

EXAMPLE 76

The effectiveness of the compounds of the invention for controlling Screw-worms, *Cochliomyia hominivorax*, a very destructive livestock pest, is demonstrated in the following test, wherein first-instar larvae of *Cochliomyia hominivorax* are permitted to feed on a mixture of ground beef (8.0 g), blood (7.0 ml), H$_2$O (2.1 ml) and

EXAMPLE 77

Determinations of LC$_{50}$ for Test Compounds Against Tobacco Budworm on Cotton Plants Young cotton plants with at least two expanded true leaves growing in 10 cm plastic pots were dipped, usually one leaf at a time, in a 65% acetone/35% water solution of test compound with agitation for 3 seconds.

The concentration of each compound in the solutions was 1.1 ppm, 2.8 ppm, 7.5 ppm, 20 ppm, 60 ppm or 150 ppm of active ingredient.

After the leaves had dried, two leaves from each of two plants were excised and placed in petri dishes (90 mm×10 mm) on moist filter paper (9 cm Whatman No. 1). Five third-instar tobacco budworm larvae were placed on each leaf and the petri dish capped. The infested dishes were then placed in a holding room with continuous light, ambient temperature of 80° F. and 50% r.h. Larval counts were made after 72 hours. Each treatment was replicated four times. Data obtained are reported in Table IX below where it can be seen that the compound of the subject invention is about 2 to 5 times more effective for the control of tobacco budworms than were the art compounds evaluated in the same test.

duce an aerosol application the insecticide solutions were pipetted (0.15 ml) into the top of a nozzle and siphoned through the atomizer nozzle. The atomized droplets are carried by an air stream (4 miles/hour) to the caged mosquitoes (25 adult females/cage) for a 4–5 second exposure. The mosquitoes were then anesthetized (3–4 seconds) with $CO_2$ and transferred to holding cages. The holding cages of treated mosquitoes were placed in a holding room at 85°±1° F. and 46±2% relative humidity. Mortality counts were made after 24 hours.

Data obtained are reported in Table X below where it can be seen that the compound of the invention was approximately four times more effective than the art compound for controlling adult *Anopheles quadrimaculatus*.

TABLE IX

Determination of $LC_{50}$ for Test Compounds Against Third-Instar Tobacco Budworms

| Compound | Dose (ppm) | Number of Insects in Test | Number of Insects Dead | $LC_{50}$ |
|---|---|---|---|---|
| 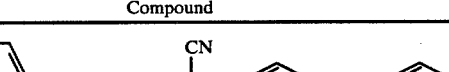 | 1.10 | 20 | 3 | 2.94 |
|  | 2.80 | 20 | 9 |  |
|  | 7.50 | 20 | 18 |  |
|  | 20.00 | 20 | 19 |  |
|  | 60.00 | 20 | 20 |  |
| 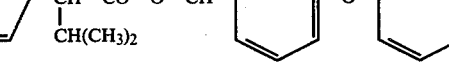 | 7.50 | 20 | 2 | 14.6 |
|  | 20.00 | 20 | 16 |  |
|  | 60.00 | 20 | 19 |  |
|  | 150.00 | 20 | 20 |  |
| Permethrin |  |  |  |  |
| 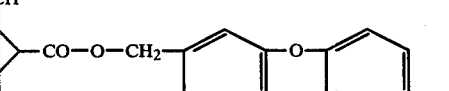 | 2.80 | 20 | 3 | 6.4 |
|  | 7.50 | 20 | 13 |  |
|  | 20.00 | 20 | 17 |  |
|  | 60.00 | 20 | 20 |  |
|  | 150.00 | 20 | 20 |  |
| South Africa 73/4462 |  |  |  |  |

EXAMPLE 78

Determination of $LC_{50}$ for Test Compounds Against Adult Mosquitoes, *Anopheles quadrimaculatus* (Say)

The compounds to be evaluated were prepared in acetone at the desired concentration in ppm. To pro-

TABLE X $LC_{50}$ Determinations of Test Compounds Against *Anopheles guadrimaculatus* Adult Females

| Compound | Concentration (ppm) | % Mortality* | Approximate (ppm) $LC_{50}$ |
|---|---|---|---|
| 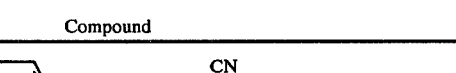 | 0.5 | 10 | 5 |
|  | 1.0 | 10 |  |
|  | 2.0 | 5 |  |
|  | 3.0 | 5 |  |
|  | 5.0 | 52 |  |
|  | 15.0 | 95 |  |
| ** 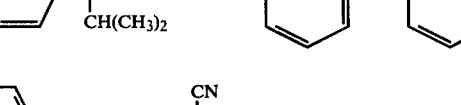 | 5.0 | (1) 10 (2) 6 | (1) 21 |
|  | 10.0 | 14    26 | (2) 18.8 |
|  | 20.0 | 66    60 |  |
|  | 40.0 | 62    78 |  |
|  | 80.0 | 92    90 |  |

*Data obtained in two different trials.
**Disclosed in South African Patent Application 73/4462.
(1) Test One.
(2) Test Two.

EXAMPLE 79

Residual Insecticidal Activity Determined for Low Volume Applications of Test Compounds Test compounds were dispersed in 65% acetone/35% water mixtures in sufficient amounts to provide 0.08 kg/ha of compound in 5.1 gallons of water. Cotton plants were then placed in a spray cabinet and sprayed with a stationary overhead sprayer as they passed beneath it.

After the leaves had dried, two leaves from each of two plants were excised and placed in petri dishes (90 mm × 10 mm) on moist filter paper (9 cm Whatman No. 1). Five third-instar tobacco budworm larvae were placed on each leaf and the petri dish capped. The infested dishes were then placed in the holding room with continuous light, ambient temperature of 80° F. and 50% r.h. Larval counts were made after 72 hours.

The remaining plants were placed under high intensity lights in the greenhouse. Leaf samples were assayed with third-instar tobacco budworm larvae after 3, 7, 10 and 14 days.

Data obtained are reported in Table XI below.

EXAMPLE 80

Ixodicidal Activity

The procedure of Example 74 is employed to demonstrate the ixodicidal activity of the compounds of the invention at 12.5, 2.5, 0.5, 0.1, 0.02 or 0.004 ppm concentrations. The results achieved are summarized in Table XII below.

TABLE XII

Percent Larval Tick Mortality of *Boophilus microplus* Larvae

| Compound | Days Post-Treatment | Percent Mortality at Conc. (ppm) | | | | | |
|---|---|---|---|---|---|---|---|
| | | 12.5 | 2.5 | 0.5 | 0.1 | 0.02 | 0.004 |
| 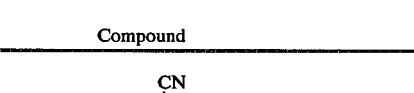 | 2 | 100 | 100 | 100 | 100 | 0 | 0 |
| | 3 | 100 | 100 | 100 | 100 | 45 | 25 |
| 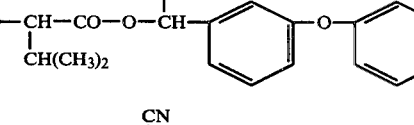 | 2 | 100 | 100 | 100 | 0 | 0 | 0 |
| | 3 | 100 | 100 | 100 | 20 | 15 | 15 |

EXAMPLE 81

The effectiveness of the compounds of the invention for controlling adult multi-host ticks, *Rhipicephalus sanguineus* (R.S.) and *Dermacentor variabilis* (D.V.), of dogs is determined in the following tests, wherein test compound is made up as described in Example 74. Sufficient compound is used to give solutions containing 100, 10 or 1 ppm of test compound.

Adult engorged female ticks are then dipped in the test solutions for 3 seconds and placed in individual containers and held for 48 hours in a room maintained at 80° F. and 50% r.h. At the end of the holding period, the ticks are examined and egg deposits counted. Engorged females that do not deposit eggs are considered dead. Data obtained are reported in Table XIII below.

TABLE XI

Residual Insecticidal Activity Against Tobacco Budworms Determined for Low Volume Spray Application on Cotton Plants

| Compound | Rate kg/ha | Days Residual Activity | | | | | | | | | |
|---|---|---|---|---|---|---|---|---|---|---|---|
| | | 0 | | 3 | | 7 | | 10 | | 14 | |
| | | 1* | 2** | 1* | 2** | 1* | 2** | 1* | 2** | 1* | 2** |
| $CF_3O$—⟨⟩—CH(CH(CH$_3$)$_2$)—CO—O—CH(CN)—⟨⟩—O—⟨⟩ | 0.08 | 95 | 0.03 | 100 | 0 | 90 | 0.03 | 90 | 0 | 80 | 0.03 |
| $Cl$—⟨⟩—CH(CH(CH$_3$)$_2$)—CO—O—CH(CN)—⟨⟩—O—⟨⟩ | 0.08 | 95 | 0.1 | 90 | 3.0 | 80 | 2.5 | 80 | 0.78 | 50 | 1.6 |
| Check | — | 0 | 92.5 | 0 | 88.5 | 0 | 87.5 | 30 | 41.3 | 0 | 67.5 |

1* = Average % Mortality 20 TBW/Point (72 Hours Mortality Count).
2** = Average % Feeding Damage/4 Replicates.

TABLE XIII

Ixodicidal Activity Against Adult Rhipicephalus sanquineus (R.S.) and Dermacentor variabilis (D.V.)

| Compound | Concentration in ppm | Percent Adult Tick Mortality R.S. | D.V. |
|---|---|---|---|
| $CF_3O$—⟨phenyl⟩—CH(CH(CH$_3$)$_2$)—COOCH(CN)—⟨phenyl⟩—O—⟨phenyl⟩ | 100 | 100 | 100 |
|  | 10 | 100 | 90 |
|  | 1 | 100 | 60 |

EXAMPLE 82

In Vitro Adult *Ctenocephalides felis* Test

In these tests, 10 adult fleas of the species *Ctenocephalides felis* are sprayed for 30 seconds with an acetone/water solution containing 100, 50, 10 or 1 ppm of the test compound. After this treatment, the fleas are maintained for 48 hours at room temperature and 80+% r.h. at 24 and 48 hours, the fleas are examined and mortality counts made. Data obtained are reported in Table XIV below.

TABLE XIV

Siphonaptericidal Activity of Test Compounds

| Compound | Hours Post-Treatment | Percent Mortality at Conc. (ppm) 100 | 50 | 10 | 1 |
|---|---|---|---|---|---|
| $F_2CHCF_2$—O—⟨phenyl⟩—CH(CH(CH$_3$)$_2$)—COOCH(CN)—⟨phenyl⟩—O—⟨phenyl⟩ | 24 | 100 | 70 | 0 | 0 |
|  | 48 | 100 | 90 | 20 | 0 |
| $F_2CHCF_2O$—⟨phenyl⟩—CH(CH(CH$_3$)$_2$)—COOCH$_2$—⟨phenyl⟩—O—⟨phenyl⟩ | 24 | 80 | 50 | 0 | 0 |
|  | 48 | 90 | 50 | 0 | 0 |

The above procedure is repeated, excepting that the concentration of the test compound is 80, 40, 20, 10, 5 or 2.5. The data are averages of two replicates at each level, except as noted.

TABLE XIVa

Siphonaptericidal Activity of Test Compound

Compound: $F_2CHO$—⟨phenyl⟩—CH(CH(CH$_3$)$_2$)—CO—O—CH(CN)—⟨phenyl⟩—O—⟨phenyl⟩

| Hours Post-Treatment | Percent Mortality at Concentration (ppm) 80 | 40 | 20 | 10 | 5 | 2.5 | 0 |
|---|---|---|---|---|---|---|---|
| 24 | 100* | 70 | 45 | 30 | 40 | 20 | 0 |

*Single Test.

EXAMPLE 83

The experiment of Example 81 is repeated, excepting that male and female adult multi-host ticks, *Rhipicephalus sanguineus* (R.S.) and *Dermacentor variabilis* (D.V.) are used. Sufficient compound is used to give solutions containing 1.0%, 0.1%, 0.01% or 0.001% of test compound. Mortality counts are made 24 and 48 hours post-treatment.

Data obtained are reported in Table XV below.

TABLE XV

Ixodicidal Activity Against Adult *Rhipicephalus sanguineus* (R.S.) and *Dermacentor variabilis* (D.V.)
(Data are averages of two replicates, except as noted.)

| Compound | Concentration in Percent | Percent Adult Tick Mortality | | | |
|---|---|---|---|---|---|
| | | R. sanguineus | | D. variabilis | |
| | | 24 Hours | 48 Hours | 24 Hours | 48 Hours |
| $F_2CHO$—⟨phenyl⟩—CH(CH(CH$_3$)$_2$)—CO—O—CH(CN)—⟨phenyl⟩—O—⟨phenyl⟩ | 1.0 | 100* | — | 100* | — |
|  | 0.1 | 100* | — | 100* | — |
|  | 0.01 | 100 | 100* | 100 | 100* |
|  | 0.001 | 100 | 100 | 65 | 65 |

*Single Test.

EXAMPLE 84

The effectiveness of the compounds of the invention for controlling face flies, Musca autumnalis, is demonstrated in the following tests, wherein day-old face fly larvae are permitted to feed on cow manure containing 0.13, 0.25 or 0.50 ppm of test compound.

Two replicates of 10 larvae per dosage level and of untreated controls are used in the evaluation.

At each level of test, an acetone solution of the appropriate amount of test compound is added to 1 kg fresh cow manure and mixed for 1 minute with an electric mixer. Manure used for unmedicated controls is processed the same way, except only acetone is added. The manure samples are divided between 4 paper souffle cups. At each level of concentration (and of controls), two cups are seeded with day-old face fly larvae. The cups are held 7 days at about 80° F. and 50% r.h. The cups are then examined for pupae, which are counted, weighed and placed in plastic vials to emerge and die. After the flies are dead, they are counted and percentages calculated. The data obtained are reported in Table XVI below.

4. A compound according to claim 2; α-cyano-m-phenoxybenzyl α-isopropyl-4-difluoromethoxyphenylacetate.

5. A compound according to claim 2; (±)-α-cyano-m-phenoxybenzyl (+)-α-isopropyl-4-difluoromethyoxyphenylacetate.

6. A compound according to claim 2; α-cyano-m-phenoxybenzyl α-isopropyl-4-trifluoromethoxyphenylacetate.

7. A compound according to claim 2; (±)-α-cyano-m-phenoxybenzyl (+)-α-isopropyl-4-trifluoromethoxyphenylacetate.

8. A compound according to claim 2; α-cyano-m-phenoxybenzyl α-ethyl-4-trifluoromethoxyphenylacetate.

9. A compound according to claim 2; m-phenoxybenzyl α-ethyl-4-trifluoromethoxyphenylacetate.

10. A compound according to claim 2; α-cyano-m-phenoxybenzyl α-ethyl-4-difluoromethoxyphenylacetate.

11. A compound according to claim 2; m-phenoxybenzyl α-isopropyl-4-trifluoromethoxyphenylacetate.

12. A compound according to claim 2; m-phenoxy-

| | | Face Flies | |
|---|---|---|---|
| Compound | Concentration in Manure ppm | Prevent Pupation % | Prevent Hatching of Pupae % |
| Control | | 0.0 | 0.0 |
| 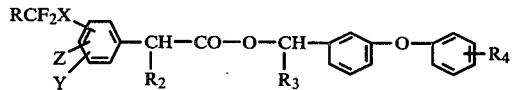 | 0.13 | 86.8 | 90.6 |
| | 0.25 | 78.9 | 84.4 |
| | 0.50 | 97.3 | 91.9 |

In Vitro Evaluation of Compounds of the Invention as Potential Feed Additives for the Control of Face Flies (Musca autumnalis) in Manure (Data are averages of two replicates.)

We claim:

1. A compound having the formula:

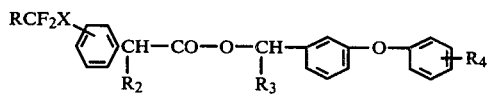

wherein $RCF_2X-$, Y and Z, are all meta or para to the carbon to which the alkanoic acid ester group is attached, and X is O, S, SO or $SO_2$; Y and Z are each H, Cl, F, Br, $NO_2$, $CH_3$ or $OCH_3$; R is H, F, $CHF_2$ or $CF_3$; $R_2$ is ethyl, n-propyl, isopropyl, isopropenyl or t-butyl; $R_3$ is H, CN or $-C\equiv CH$, and $R_4$ is H, F, Cl, $CH_3$ or $OCH_3$ or the optical isomers thereof.

2. A compound according to claim 1 of the formula:

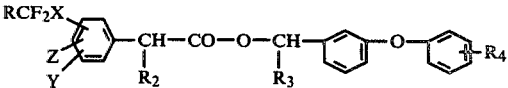

wherein $RCF_2X-$ is meta or para to the carbon to which the alkanoic acid ester group is attached; R is H or F; X is O or S; $R_2$ is ethyl, n-propyl or isopropyl; $R_3$ is H, CN or $-C\equiv CH$ and $R_4$ is H, F, Cl, $CH_3$ or $OCH_3$.

3. A compound according to claim 2 wherein R is H or F; $R_2$ is isopropyl; $R_3$ is CN, X is O and $R_4$ is H or F.

benzyl α-isopropyl-4-difluoromethoxyphenylacetate.

13. A compound according to claim 2; α-cyano-m-phenoxybenzyl α-isopropyl-4-trifluoromethylthiophenylacetate.

14. A compound according to claim 2; α-cyano-m-(p-fluorophenoxy)benzyl α-isopropyl-4-difluoromethoxyphenylacetate.

15. A compound according to claim 2; α-cyano-m-(p-fluorophenoxy)benzyl α-isopropyl-4-trifluoromethoxyphenylacetate.

16. A compound according to claim 1; α-cyano-m-phenoxybenzyl α-isopropyl-3-chloro-4-difluoromethoxyphenylacetate.

17. A method for controlling insects and acarina comprising contacting the insects and acarina, their habitat, breeding grounds or feed, with an insecticidally or acaricidally effective amount of a compound of the formula:

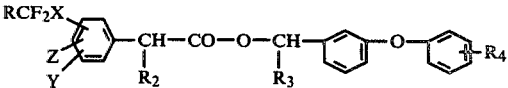

wherein $RCF_2X-$, Y and Z, are all meta or para to the carbon to which the alkanoic acid ester group is attached, and X is O, S, SO or $SO_2$; Y and Z are each H, Cl, F, Br, $NO_2$, $CH_3$ or $OCH_3$; R is H, F, $CHF_2$ or $CF_3$; $R_2$ is ethyl, n-propyl, isopropyl, isopropenyl or t-butyl;

$R_3$ is H, CN or —C≡CH, and $R_4$ is H, F, Cl, $CH_3$ or $OCH_3$ or the optical isomers thereof.

18. A method according to claim 17 wherein the compound is of the formula:

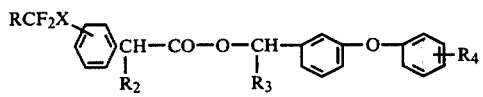

wherein $RCF_2X$ is meta or para to the carbon to which the alkanoic acid ester group is attached; R is H or F; X is O or S; $R_2$ is ethyl, n-propyl or isopropyl; $R_3$ is H, CN or —C≡CH and $R_4$ is H, F, Cl, $CH_3$ or $OCH_3$.

19. A method according to claim 18 wherein the compound is α-cyano-m-phenoxybenzyl α-isopropyl-4-difluoromethoxyphenylacetate.

20. A method according to claim 18 wherein the compound is (±)-α-cyano-m-phenoxybenzyl (+)-α-isopropyl-4-difluoromethoxyphenylacetate.

21. A method according to claim 18 wherein the compound is (±)-α-cyano-m-phenoxybenzyl (+)-α-isopropyl-4-trifluoromethoxyphenylacetate.

22. A method according to claim 18 wherein the compound is m-phenoxybenzyl α-ethyl-4-trifluoromethoxyphenoxyacetate.

23. A method according to claim 18 wherein the compound is m-phenoxybenzyl α-isopropyl-4-trifluoromethoxyphenylacetate.

24. A method for the systemic control of insects and acarina that feed on the body fluids of livestock and domestic animals comprising orally or parenterally administering to the animal host a systemically effective amount of a compound having the formula:

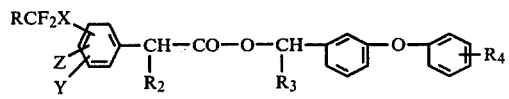

wherein $RCF_2X$—, Y and Z, are all meta or para to the carbon to which the alkanoic acid ester group is attached, and X is O, S, SO or $SO_2$; Y and Z are each H, Cl, F, Br, $NO_2$, $CH_3$ $OCH_3$; R is H, F, $CHF_2$ or $CF_3$; $R_2$ is ethyl, n-propyl, isopropyl, isopropenyl or t-butyl; $R_3$ is H, CN or —C≡CH, and $R_4$ is H, F, Cl, $CH_3$ or $OCH_3$ or the optical isomers thereof.

25. A method according to claim 24 wherein X is S or O.

26. A method according to claim 25 wherein the compound is orally administered to the host animal.

27. A method according to claim 25 wherein the compound is parenterally administed to the host animal.

28. An insecticidal composition comprising a compound of the formula:

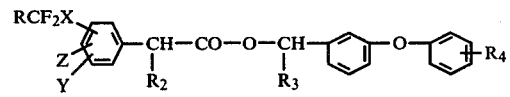

wherein $RCF_2X$—, Y and Z, are all meta or para to the carbon to which the alkanoic acid ester group is attached, and X is O, S, SO or $SO_2$; Y and Z are each H, Cl, F, Br, $NO_2$, $CH_3$ or $OCH_3$; R is H, F, $CHF_2$ or $CF_3$; $R_2$ is ethyl, n-propyl, isopropyl, isopropenyl or t-butyl; $R_3$ is H, CN or —C≡CH, and $R_4$ is H, F, Cl, $CH_3$ or $OCH_3$ or the optical isomers thereof; an emulsifying agent, a surfactant and a solvent.

29. A composition according to claim 28 wherein X of the formula is S or O.

* * * * *